(12) United States Patent  
Peterson

(10) Patent No.: US 10,399,964 B2  
(45) Date of Patent: Sep. 3, 2019

(54) COUMARIN-LINKED TAXANES FOR DETECTION AND CIRCUMVENTION OF CELLULAR EFFLUX

(71) Applicant: The University of Kansas, Lawrence, KS (US)

(72) Inventor: Blake R. Peterson, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 15/940,152

(22) Filed: Mar. 29, 2018

(65) Prior Publication Data

US 2018/0282314 A1 Oct. 4, 2018

Related U.S. Application Data

(60) Provisional application No. 62/478,954, filed on Mar. 30, 2017.

(51) Int. Cl.
   *C07D 407/12* (2006.01)
   *A61P 35/00* (2006.01)
   *G01N 33/58* (2006.01)

(52) U.S. Cl.
   CPC ........... *C07D 407/12* (2013.01); *A61P 35/00* (2018.01); *G01N 33/582* (2013.01)

(58) Field of Classification Search
   CPC ...... C07D 407/12; A61P 35/00; G01N 33/582
   See application file for complete search history.

(56) References Cited

U.S. PATENT DOCUMENTS

| | | |
|---|---|---|
| 2015/0274701 A1 | 10/2015 | Taran et al. |
| 2016/0095941 A1 | 4/2016 | Brahmbhatt et al. |

FOREIGN PATENT DOCUMENTS

| | | |
|---|---|---|
| WO | 9719938 A1 | 1/1997 |
| WO | 2003008965 A1 | 1/2003 |
| WO | 2014057201 A1 | 4/2014 |
| WO | 2016051389 A1 | 4/2016 |
| WO | 2015111349 A1 | 7/2016 |

OTHER PUBLICATIONS

Lee et al., Synthesis of a Fluorescent Analogue of Paclitaxel That Selectively Binds Microtubules and Sensitivity Detects Efflux by P-Glycoprotein.*

* cited by examiner

*Primary Examiner* — Alexander R Pagano
*Assistant Examiner* — Ebenezer O Sackey
(74) *Attorney, Agent, or Firm* — Maschoff Brennan

(57) ABSTRACT

A compound can be a fluorescent taxane derivative having a structure of Formula 1, salt, stereoisomer, tautomer, polymorph, or solvate thereof. Formula 1 can be defined as: L, L-NH, or L-NH—C═O is a linker; and R is a substituent, where —OH, —O⁻, —NH₂, and NH—CH₃ are examples. Examples of linkers can include glycine, beta-alanine, gamma-aminobutyric acid (GABA). Pharmaceutical compositions can include the compound and a pharmaceutically acceptable carrier, and may be configured for intravenous injection. The fluorescent taxane derivative can be used to treat cancer and non-cancer diseases. The fluorescent taxane derivative can be used to monitor cellular efflux and determine whether a cell will efflux paclitaxel.

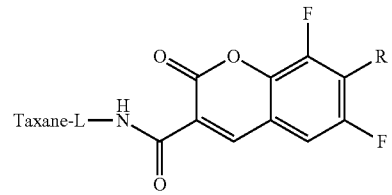

Formula 1

21 Claims, 12 Drawing Sheets

PB-NH$_2$-Gly-Taxol (R=H)
PB-NHMe-Gly-Taxol (R=Me)

COUMARIN-LINKED TAXANES FOR DETECTION AND CIRCUMVENTION OF CELLULAR EFFLUX

CROSS-REFERENCE

This patent application claims priority to U.S. Provisional Application No. 62/478,954 filed Mar. 30, 2017, which provisional is incorporated herein by specific reference in its entirety.

GOVERNMENT RIGHTS

This invention was made with government support under GM103638 awarded by the National Institutes of Health. The government has certain rights in the invention.

BACKGROUND

Paclitaxel (Taxol®) is a natural product that can be isolated from the bark of the yew tree *Taxus brevifolia*. Paclitaxel has become an effective treatment for various types of cancers, such as ovarian, breast, and lung. Taxol® has the biological activity of binding the protein β-tubulin and stabilizing microtubules in the cytosol. Additionally, paclitaxel inhibits microtubule polymerization dynamics and can trigger cellular death via apoptosis. Although paclitaxel is widely used as a therapeutic, some mechanisms underlying its selective cytotoxicity towards cancer cells remain unknown. Paclitaxel and related compounds, such as taxanes and taxoids, can exhibit antimitotic activity against rapidly dividing cancer cell lines and xenografts that double every 1-12 days, suggesting that effects against rapidly proliferating cells might provide selectivity against tumors in human patients. However, these types of compounds also show major effects against slow growing tumors (median doubling time of ~147 days) in patients, while sparing rapidly proliferating normal cells in bone marrow, gut, and other tissues.

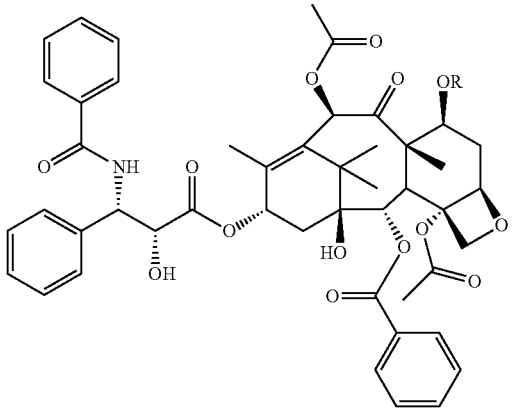

Paclitaxel, R = H

Fluorescent analogues of paclitaxel have been used for studying their anticancer effects. An example of such a compound termed Flutax-2® includes paclitaxel linked at the 7-position through a β-Ala ester to the fluorophore Oregon Green (OG), as shown below. The term Flutax-2® has also been used to describe a related fluorescent probe where paclitaxel is linked to OG via an L-Ala ester (termed here Flutax-2® (L-Ala)). The side-chain of Taxol® has also been linked to the BODIPY fluorophore, but these probes are generally not considered suitable for imaging of living cells.

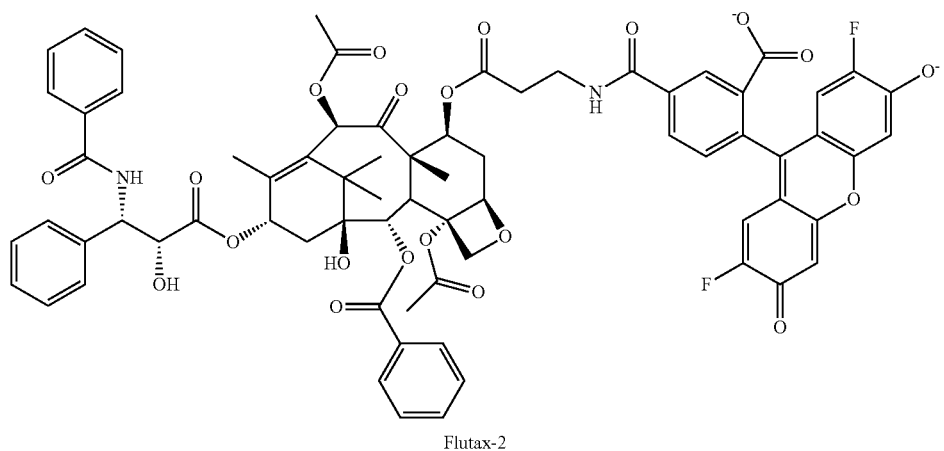

Flutax-2

At physiological pH, OG exists as a highly polar dianion. In Flutax-2, this increases the polarity of paclitaxel by almost 1000-fold, which alters its calculated octanol-water distribution/partition coefficient from c Log $D_{pH7.4}$=2.9 (paclitaxel) to c Log $D_{pH7.4}$=0.0 (Flutax-2®). Given that most small molecule drugs are generally moderately hydrophobic (c Log $D_{pH7.4}$~2), which facilitates passive diffusion across membranes, Flutax-2® differs substantially from paclitaxel under physiological conditions.

Therefore, it may be advantageous to provide more paclitaxel-like fluorescent probes.

SUMMARY

In one embodiment, the present invention includes taxanes (e.g., paclitaxel is a taxane, and other taxoids are taxanes) linked to a coumarin-derived fluorophore, such as Pacific Blue (PB) or an analogue of PB. Additionally, the taxane-PB-fluorophores can be used in methods similarly to paclitaxel or other fluorescent taxanes. The taxanes may be linked to the coumarin-derived fluorophore at any of carbons 3, 4, 5, 6, 7, or 8 as shown below, and the other carbons may or may not include a substituent. In one example, the taxane is linked to the coumarin-derived fluorophore through carbon 3. In another example, the coumarin-derived fluorophore may include substituents at carbons 6, 7, and 8. In another example, the coumarin-derived fluorophore may include halogens, such as fluorine at carbons 6 and 8. In another example, the coumarin-derived fluorophore may include a substituent at carbon 7, such as a hydroxyl, amine, alkyl-amine, or the like.

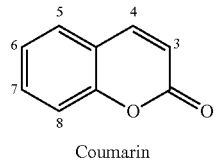

Coumarin

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
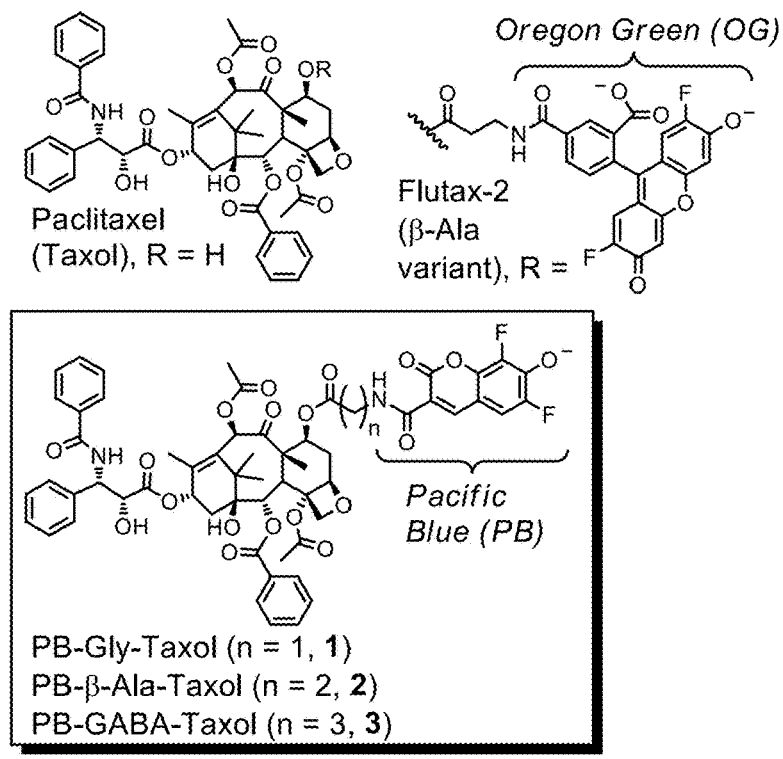
FIG. 1 shows the structures of paclitaxel, Flutax-2®, and taxane PB fluorophore Compounds 1-3.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes taxanes (e.g., paclitaxel is a taxane, and other taxoids are derivatives of taxanes) linked to a fluorophore derived from coumarin (2H-chromene-2-one), such as Pacific Blue (PB) or derivative or analogue of PB (PB derivative). For the purposes of this disclosure, taxanes are intended to also cover taxoids. In this application the abbreviation PB can refer to any coumarin-derived structure. As such, the present disclosure provides taxane PB fluorophores, referred to herein as TPBFs, which include any taxane that is conjugated to a coumarin so as to retain the properties of the taxane and the coumarin. In one aspect, the taxanes are conjugated to a fluorescent coumarin or coumarin-derivative through a linker, which are also referred to under the term TPBF.

An example of a taxane is paclitaxel, which can be conjugated to the PB or PB derivative through a linker. The resulting paclitaxel PB conjugate (e.g., including coumarins, paclitaxel PB, and paclitaxel PB derivatives) can be substantially smaller and less polar than Flutax-2® (c Log $D_{pH7.4}$=2.0 for PB-Gly-Taxol, which is Compound 1 provided herein, see FIG. 1). The other taxanes may be linked through any of the linkers to the PB fluorophore to provide a compound that has the properties of the taxane, such as paclitaxel properties, and the fluorescent property.

In one embodiment, the TPBF compounds described herein can be used to detect inhibitors of cellular efflux transporters and other agents that affect these proteins. These transporters are of interest for drug development projects. Existing substrates of efflux transporters, such as P-glycoprotein (P-gp), lack sensitivity. The TPBFs described herein are sensitive substrates of this efflux transporter and bind microtubules in living cells. The compounds have compatibility with flow cytometry, and other fluorescent detection methods, and can be used to detect low levels of P-gp activity undetectable with existing substrates. The TPBFs have various uses such as those described herein, such as studying the P-gp activity, among others.

Taxoids are a class of derivatives or analogues of paclitaxel. The taxoids may have anticancer chemotherapeutic properties as well as other properties of paclitaxel. As used herein, taxoids may be synonymous with taxanes, and thereby the taxanes recited herein include the taxoids. The taxoids class and the taxanes class both include paclitaxel and docetaxel, among others.

Pacific Blue is often provided as the Pacific Blue succinimidyl ester, as shown below, for reaction with other compounds. During coupling chemistry to couple the Pacific Blue to a taxane, the procedure results in the Pacific Blue structure provided below (Pacific Blue amide), which is then linked via the nitrogen atom through a linker (e.g., L) to the taxane as shown. It should be recognized that the oxygen anion of Pacific Blue may also be present as a protonated phenol (—OH), and thereby the structures of Pacific Blue are also intended to cover the protonated form. For the purposes of clarity, the Pacific Blue anion will be used to describe the presently technology; however, the descriptions are also affirmatively indicated to also refer to the structures including the protonated phenol species and other protonated and deprotonated forms and salts.

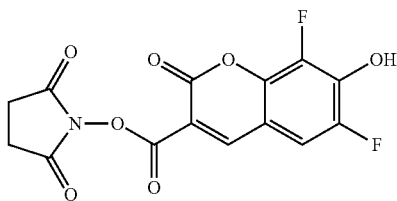 [SMILES: O=C(ON1C(=O)CCC1=O)c1cc2cc(F)c(O)c(F)c2oc1=O]

Pacific Blue succinimidyl ester

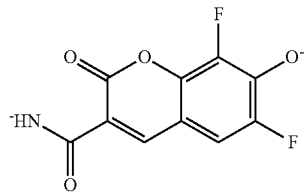 [SMILES: [NH-]C(=O)c1cc2cc(F)c([O-])c(F)c2oc1=O]

Pacific Blue amide derivative shown as the anion (the deprotonated form that predominates at physiological pH)

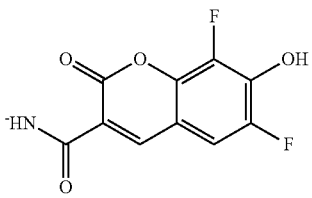 [SMILES: [NH-]C(=O)c1cc2cc(F)c(O)c(F)c2oc1=O]

Pacific Blue amide derivative as the phenol (protonated form that may be isolated during synthesis)

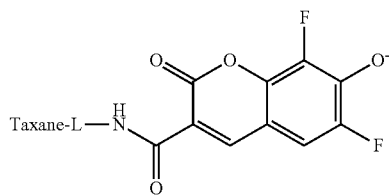

Taxane Pacific Blue anion

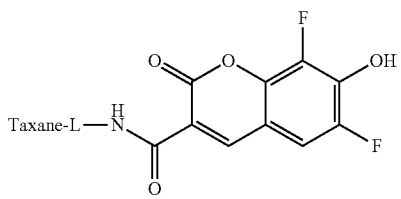

Taxane Pacific Blue phenol

Now, it has been found that the Pacific Blue may be derivatized, such as at the R group shown in Formula 1 below in order to provide improved TPBFs. The R group may be any substituent, such as reasonable substituents which are recited herein. The R group may vary as described below. In one example, the R group is hydroxyl (phenol). Another example is when the R group includes a nitrogen, and thereby is a primary amine (—$NH_2$ or aniline) or alkyl secondary amine (—NH-alkyl), or alkyl tertiary amine (—N(alkyl)$_2$). In another example, the R group includes a nitrogen that is then linked to another substituent, and thereby is a substituted secondary amine (—$NH_2$—R1), or di-substituted tertiary amine (—N(R1)$_2$ or —NR1R2), where the R1 group and/or R2 group is any substituent, whether the same or different, such as shown in Formula 2.

Formula 1

Formula 2

In one embodiment, the present technology includes a TPBF compound, which is a fluorescent taxane derivative, having a structure of Formula 1 or Formula 2 (shown above), salt, stereoisomer, tautomer, polymorph, or solvate thereof. In one aspect, the L, L-NH, or L-NH—C=O of Formula 1 or Formula 2 is a linker. The R group can be any reasonable substituent.

In one embodiment, the R is selected from:

(a) —$NH_2$, —NH-alkyl, —N(alkyl)$_2$, —$NH_2$—R1, —N(R1)$_2$ or —NR1R2, or combination thereof;

(b) —C(O)R1a, —C(O)CH(NR1bR1c)R1a, —C(O)CH(N(R1c)C(O)R1b)R1a, —C(O)CH(N(R1c)C(O)OR1b)R1a, —C(O)CH(N(R1c)C(O)NR1bR1d)R1a, —C(O)OR1a, —C(O)NR1bR1c, —C(NR1a)NR1bR1c, —P(O)(OR1a)R1d, —CH2P(O)(OR1a)R1d, —S(O)R1a, —S(O)2R1a, —S(O)NR1bR1c, or —S(O)2NR1bR1c;

(c) $C_1$-$C_{24}$ alkyl, $C_2$-$C_{24}$ alkenyl, $C_2$-$C_{24}$ alkynyl, $C_3$-$C_{20}$ cycloalkyl, $C_5$-$C_{20}$ aryl, $C_5$-$C_{20}$ polyaryl, $C_6$-$C_{24}$ alkaryl, $C_6$-$C_{24}$ aralkyl, heteroaryl, heterocyclyl, hydrogen, halo, oxygen anion, hydroxyl anion, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl, $C_6$-$C_{20}$ arylcarbonyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ aryl carbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino, or combinations thereof; as well as combinations of (a), (b), and (c).

In one embodiment, under Formula 1 or Formula 2, the R group is optionally substituted by a substituent Q, which substituent Q is defined as R.

In one embodiment, R1, R2, R1a, R1b, R1c, or R1d are each independently as defined for R or independently hydrogen. In one aspect, R is not hydrogen. In one aspect, one or both of R1 and R2 can be hydrogen. In one aspect, one of R1 and R2 can be hydrogen, and the other an alkyl, such as methyl, ethyl, propyl, butyl, pentyl or the like, whether straight or branched or cyclic.

In one embodiment, the linker is selected from: $C_1$-$C_{24}$ alkyl, $C_2$-$C_{24}$ alkenyl, $C_2$-$C_{24}$ alkynyl, $C_3$-$C_{20}$ cycloalkyl, $C_5$-$C_{20}$ aryl, $C_5$-$C_{20}$ polyaryl, $C_6$-$C_{24}$ alkaryl, $C_6$-$C_{24}$ aralkyl, heteroaryl, heterocyclyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl, $C_6$-$C_{20}$ arylcarbonyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ aryl carb onato, carboxy, carboxylato, carb amoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, amino, amino acid, essential amino acid, non-essential amino acid, L-amino acid, D-amino acid, glycine, beta-alanine, gamma-aminobutyric acid (GABA), mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, or combinations thereof.

In one aspect, the linker may be one of linkers L1, L2, L3, or L4 as shown below, wherein n is an integer. It should be recognized that the linker extends between the taxane and the fluorescent PB fluorophore, and thereby the determination of the end of the taxane and beginning of the linker as well as the end of the linker and beginning of the PB fluorophore may be defined. Accordingly, linkers L1, L2, L3, or L4 account for the different possibilities of the end of the taxane and beginning of the linker as well as the end of the linker and beginning of the PB fluorophore. Preferably, the linker is L4 so that the taxane is considered to include the terminal oxygen that links to the linker, and the PB fluorophore is considered to include the carboxyl (C=O). For the linker, n may be 1, 2, 3, 4, 5, 6, 7, 8, 9, 10, 11, 12, 13, 14, 15, 16, 17, 18, 19, 20, 21, 22, 23, or 24. The linker may be attached to carbon atoms 3, 4, 5, 6, 7, or 8 of the coumarin.

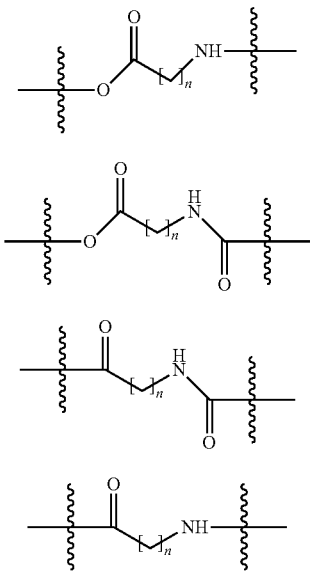

In one embodiment, the linker is selected from glycine, beta-alanine, gamma-aminobutyric acid (GABA). In one example, the linker is glycine.

In one embodiment, R is selected from —O⁻, —OH, —NH₂, —NH-alkyl, —N(alkyl)₂, —NH₂—R1, —N(R1)₂ or —NR1R2; R1 is $C_1$-$C_{24}$ alkyl; and R2 is hydrogen or $C_1$-$C_{24}$ alkyl. In one aspect, the R1 or alkyl is methyl and R2 is hydrogen. In one aspect, R is selected from —O⁻, —OH, —NH-methyl. In one aspect of this embodiment for R, the linker is selected from glycine, beta-alanine, gamma-aminobutyric acid (GABA).

In one embodiment, the fluorescent taxane derivative is selected from Formula 3, Formula 4, or Formula 5 or salt, stereoisomer, tautomer, polymorph, or solvate thereof. The linker can be any linker described herein. Also, the taxane can be any taxane, such as those described herein or otherwise known.

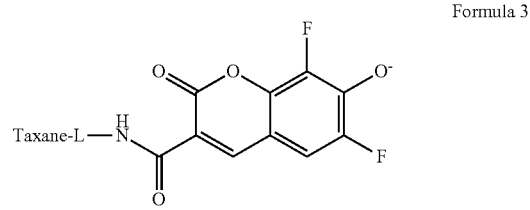

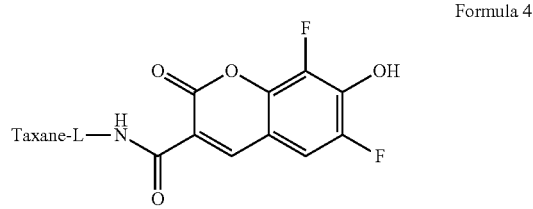

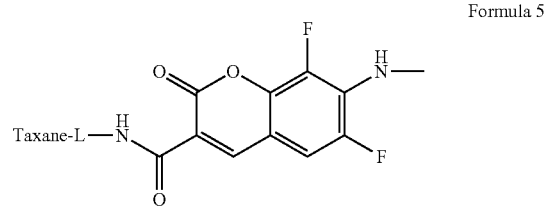

In one embodiment, the fluorescent taxane derivative is selected from Formula 6, Formula 7, or Formula 8 or salt, stereoisomer, tautomer, polymorph, or solvate thereof. The "n" of the linker can be any integer described herein. Also, the taxane can be any taxoid, such as those described herein or otherwise known.

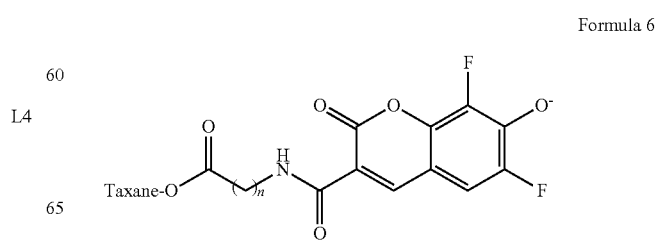

-continued

Formula 7

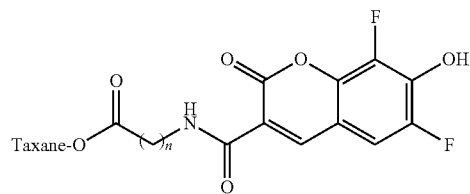

Formula 8

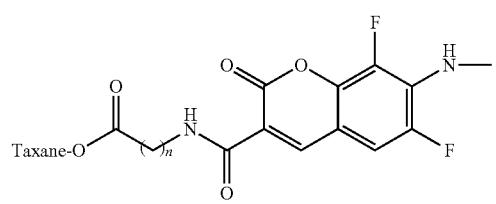

While the taxane can be any known or developed taxane, such as those described herein, certain taxanes are provided herein as examples, including Paclitaxel, Baccatin III, 10-Deacetylbaccatin III, and Docetaxel, as shown below. The point of conjugation of the taxanes are shown.

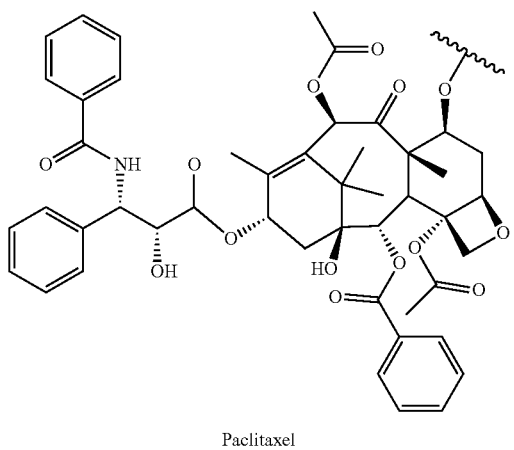

Paclitaxel

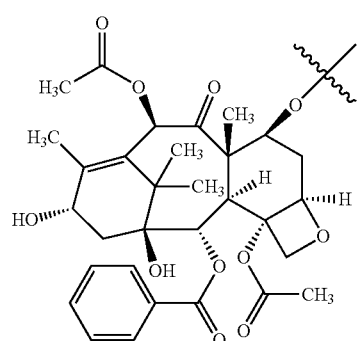

Baccatin III

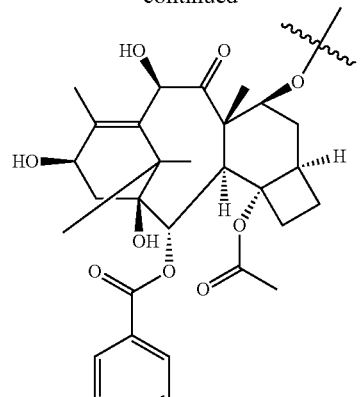

10-Deacetylbaccatin III

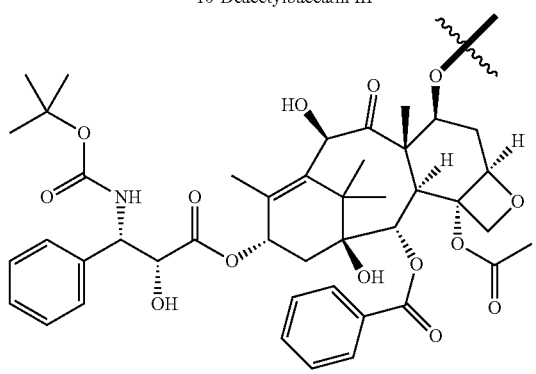

Docetaxel

In one embodiment, the linker is one of L1, L2, L3, or L4 and R is selected from —O⁻ (oxygen anion), —OH, —NH$_2$, —NH-alkyl, —N(alkyl)$_2$, —NH$_2$—R1, —N(R1)$_2$ or —NR1R2; R1 is $C_1$-$C_{24}$ alkyl; and R2 is hydrogen or $C_1$-$C_{24}$ alkyl.

In one embodiment, R is selected from —O⁻, —OH, —NH-methyl; and the linker is selected from glycine, beta-alanine, gamma-aminobutyric acid (GABA). In one embodiment, it is preferred that the linker is glycine.

Optionally, the linker between the taxane or taxoid and the pacific blue can be substituted with a substituent. Optionally, either fluorine of the pacific blue or the OH of the pacific blue or any other hydrogen of the coumarin core structure can be substituted with different substituents. These substituents can independently include hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, aryl carbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido arylamido, imino, alkylimino, arylimino, nitro, nitroso, sulfo, sulfonato, alkylsulfanyl, arylsulfanyl, alkylsulfinyl, arylsulfinyl, alkylsulfonyl, aryl sulfonyl, phosphono, phosphonato, phosphinato, phospho, phosphino, any with or without hetero atoms, derivatives thereof, and combinations thereof. Optionally, the linker between the taxane or taxoid and the pacific blue substance can include straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, carbamates, amides, esters, amino acids, peptides, polypeptides, derivatives thereof, substituted or unsubstituted, or combinations thereof as well as other well-known chemical substituents.

In another option, the linker between the taxane or taxoid and the coumarin can be substituted with a substituent, and/or either fluorine (F) or other hydrogen (H) atom or the hydroxyl (OH) of the coumarin core structure of the Pacific Blue coumarin derivative shown can be substituted with different substituents. These substituents can be independently any one or more of the substituents selected from the group of hydrogen, $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl (including $C_2$-$C_{24}$ alkylcarbonyl (—CO-alkyl) and $C_7$-$C_{20}$ arylcarbonyl (—CO-aryl)), acyloxy (—O-acyl), $C_2$-$C_{24}$ alkoxycarbonyl (—(CO)—O-alkyl), $C_7$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_7$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), di-substituted arylcarbamoyl (—(CO)—NH-aryl)$_2$, thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-substituted arylthiocarbamoyl (—(CS)—NH-aryl), di-substituted arylthiocarbamoyl (—(CS)—NH-aryl)$_2$, carbamido (—NH—(CO)—NH$_2$),), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH—(CO)—N($C_1$-$C_{24}$ alkyl)$_2$), mono-substituted aryl carbamido (—NH—(CO)—NH-aryl), di-substituted aryl carbamido (—NH—(CO)—N-(aryl)$_2$) cyano(—C≡N), isocyano (—N$^+$≡C$^-$), cyanato (—O—C≡N), isocyanato (—O—N$^+$≡C$^-$), thiocyanato (—S—C≡N), isothiocyanato (—S—N$^-$≡C$^-$), azido (—N═N$^+$═N$^-$), formyl (—(CO)—H), thioformyl (—(CS)—H), amino (—NH$_2$), mono- and di-($C_1$-$C_{24}$ alkyl)-substituted amino, mono- and di-($C_6$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR═NH where R is hydrogen, $C_1$-$C_{24}$ alkyl, $C_6$-$C_{20}$ aryl, $C_7$-$C_{24}$ alkaryl, $C_7$-$C_{24}$ aralkyl, etc.), alkylimino (—CR═N(alkyl), where R=hydrogen, $C_1$-$C_{24}$ alkyl, aryl, alkaryl, aralkyl, etc.), arylimino (—CR═N(aryl), where R=hydrogen, alkyl, aryl, alkaryl, etc.), nitro (—NO$_2$), nitroso (—NO), sulfonic acid (—SO$_2$—OH), sulfonato (—SO$_2$—O$^-$)' $C_1$-$C_{24}$ alkylsulfanyl (—S-alkyl; also termed "alkylthio"), $C_6$-$C_{20}$ arylsulfanyl (—S-aryl; also termed "arylthio"), $C_1$-$C_{24}$ alkylsulfinyl (—(SO)-alkyl), $C_6$-$C_{20}$ arylsulfinyl (—(SO)-aryl), $C_1$-$C_{24}$ alkylsulfonyl (—SO$_2$-alkyl), $C_6$-$C_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$), any with or without hetero atoms (e.g., N, O, P, S, or other) where the hetero atoms can be substituted (e.g., hetero atom substituted for carbon in chain or ring) for the carbons or in addition thereto (e.g., hetero atom added to carbon chain or ring) swapped, derivatives thereof, and combinations thereof.

Additionally, the coumarin-derived fluorophore may be substituted at one or more of the carbon atoms 3, 4, 5, 6, 7, or 8 of the coumarin, which may include the taxane being attached to one of carbon atoms 3, 4, 5, 6, 7, or 8 of the coumarin, and no substituents or one or more substituents being attached to one or more of the other carbon atoms of carbon atoms 3, 4, 5, 6, 7, or 8 of the coumarin. Accordingly, the present technology includes fluorescent coumarin derivative, having a structure of Formula 9, salt, stereoisomer, tautomer, polymorph, or solvate thereof. The R3, R4, R5, R6, R7, and/or R8 groups can be any reasonable substituent so long as one of R3, R4, R5, R6, R7, and/or R8 is a taxane and linker (e.g., L) linked thereto (e.g., taxane-L-). The taxane can be any taxane, such as the taxanes shown herein. The linker can be any linker, such as the linker being one of linkers L1, L2, L3, or L4 as shown here or a linker as defined herein. The R3, R4, R5, R6, R7, and/or R8 groups can be as defined for R, R2, and R2, and may be optionally substituted by a substituent Q, which substituent Q is the same as defined as R.

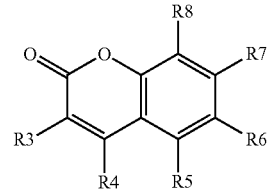

Formula 9

In one embodiment, the present technology includes a pharmaceutical composition having: the compound of one of the embodiments; and a pharmaceutically acceptable carrier. The pharmaceutically acceptable carrier can be any known carrier, such as those described herein. The pharmaceutical composition can be used in any of the methods described herein or for any use of a taxane, such as paclitaxel. Additionally, the use as a pharmaceutical composition allows for imaging and visualization of the localization of the taxane by the fluorescence of the PB fluorophore.

In one embodiment, the taxane PB fluorophore can be used in a method of treating cancer. Such a method can include administering the compound of one of the embodiments to a subject having cancer. For example, the cancer is Kaposi sarcoma, cervical cancer, pancreatic cancer, ovarian, breast, and/or lung cancer; however, the compound may be useful for other cancers. Often, the administration of the pharmaceutical composition is intravenous injection; however, other modes of administration such as oral administration are known or may be developed. In one embodiment, due to a possible allergic reaction, the compound can be co-administered with an anti-allergy medicine.

Beneficially, the fluorescent nature of the taxane PB fluorophore may be used for determining the effectiveness of the treatment by obtaining biological samples, such as via a biopsy of the cancer, including a tumor and/or surrounding tissue to determine whether the distribution within the biological sample. Samples that have higher amounts in the tumors may be more effective. Also, the protocol of visualizing the fluorophore can be used in any method of administering the compound to a subject, and obtaining biological samples from various locations, organs, tissues, or anatomical body parts. This may also be used to monitor tumor metastasis. As such, the translocalization of cancerous cells may be monitored, such as visualized, by monitoring the movement of cancer cells in a body or identifying different location of the cancer cells within the body (e.g., via biopsy or fluorescent imaging catheter).

The biological activity of paclitaxel arrests cell cycle and induces cell death by stabilizing microtubules and interfering with microtubule disassembly in cell division. Recently, it has been found that low-dose paclitaxel may be used in treating non-cancer diseases, such as skin disorders, renal and hepatic fibrosis, inflammation, axon regeneration, limb salvage, and coronary artery restenosis. Thus, the present technology may be used in method for treating one or more of these non-cancer diseases.

In one embodiment, a method of studying microtubules can include: contacting the compound of one of the embodiments with microtubules within a cell or extracted from cells; and/or monitoring the functionality of microtubules in cells. In one aspect, the method can include visualizing microtubules from fluorescence of the compound bound to microtubules.

In one embodiment, a method of studying a P-glycoprotein can include: studying interactions with purified P-glycoprotein, or in cell(s) containing P-glycoprotein, with the compound of one of the embodiments; and monitoring efflux or no efflux of one or more substances from a cell having the P-glycoprotein. In one aspect, the method can include visualizing the efflux or no efflux of the compound from the cell from changes in fluorescence of the compound. In one aspect, this protocol can be used to determine whether or not a cell, such as a cancerous cell, can efflux the taxane PB fluorophore. If the cell cannot efflux the taxane PB fluorophore, then paclitaxel may be more suitable for treatment of the cancerous cell. If the cell can efflux the taxane PB fluorophore, then paclitaxel may not be as suitable for treatment of the cancerous cells. Such monitoring can be done with a cell culture of a biopsy, in vitro, ex vivo, or in vivo. Taxane PB compounds may be used for high-throughput screening or high-content screening or other screening assays for the discovery of inhibitors or modulators of P-glycoprotein or other efflux transporters that use them as substrates.

Whereas monitoring the efflux of the taxane PB fluorophore may be used for cancerous cells, it may also be used with any cells that are involved with a non-cancerous disease state of skin disorders, renal and hepatic fibrosis, inflammation, axon regeneration, limb salvage, and coronary artery restenosis. In one aspect, this protocol can be used to determine whether or not a cell can efflux the taxane PB fluorophore. If the cell cannot efflux the taxane PB fluorophore, then paclitaxel may be suitable to treat the cell. If the cell can efflux the taxane PB fluorophore, then paclitaxel may not be suitable to treat the cells. Such monitoring can be done with a cell culture of a biopsy, in vitro, ex vivo, or in vivo.

These compounds can be prepared as pharmaceutical compositions. Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (e.g., Tween® and Cremophor EL), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), dioleysl-phosphotidyl-ethanolamine (DOPE), and liposomes. Such compositions should contain a therapeutically effective amount of the compound, together with a suitable amount of carrier so as to provide the form for direct administration to the patient.

The compositions described herein can be administered for example, by parenteral, intravenous, subcutaneous, intramuscular, intracranial, intraorbital, ophthalmic, intraventricular, intracapsular, intraspinal, intracisternal, intraperitoneal, intranasal, aerosol or oral administration. Common carriers or excipients can be used for preparing pharmaceutical compositions designed for such routes of administration.

Experimental

FIG. 1 shows the structures of paclitaxel, Flutax-2®, and taxane PB fluorophores Compounds 1-3.

Figure 1A:
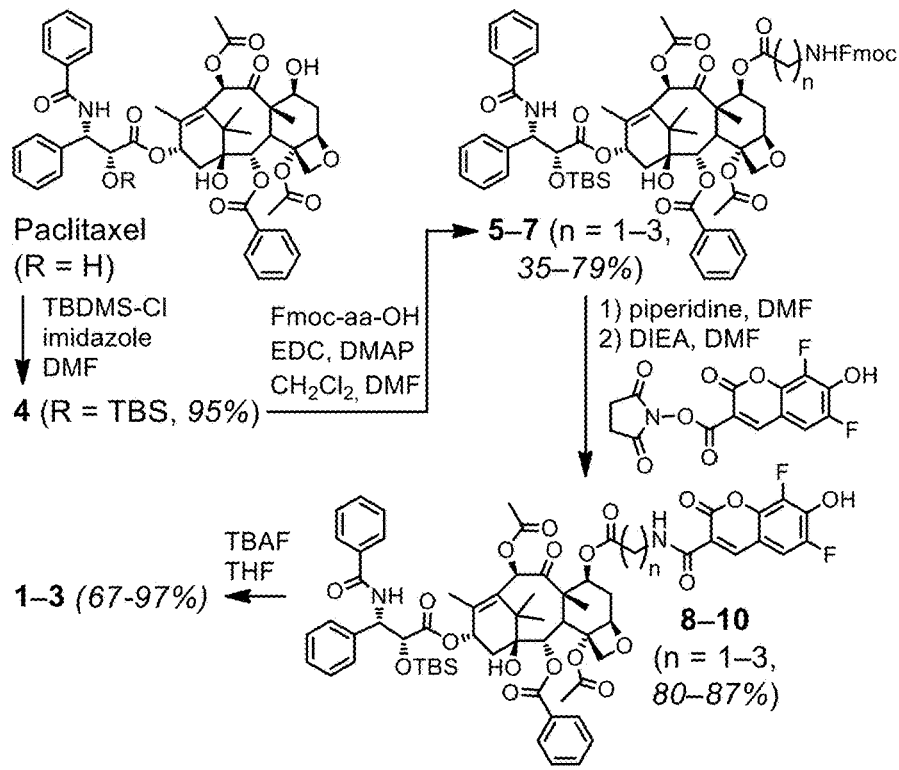
FIG. 1A shows reaction Scheme 1 to prepare the compounds of FIG. 1.

The compounds described herein may be synthesized via the protocol in Scheme 1, which protocol may be modified depending on the desired taxane PB fluorophore to be prepared. Scheme 1 is shown in FIG. 1A. The compounds are identified by the compound numbers. Since taxoids modified at the 7-position can retain high affinity for microtubules, PB was linked at this position by amino acids that differ subtly in the number of methylenes between the amine and the carbonyl. Optical spectroscopy confirmed that Compounds 1-3 are similar to PB, whereas Flutax-2® is similar to OG. It should be noted that the reaction in Scheme 1 is shown to produce the Compounds 1-3 having the R group under Formula 1 being the hydroxyl; however, it should be recognized that the hydrogen of the hydroxyl may be deprotonated so as to be the structures shown in FIG. 1. Accordingly, the same Compounds 1-3 may have the R group as the hydroxyl or oxygen anion. FIG. 1A shows the reaction Scheme 1 that is performed to prepare the taxane (e.g., paclitaxel) into the taxane PB fluorophores under Formula 1. Also, it should be recognized that any taxane may be prepared as shown to be the reagent in order to prepare a wide variety of taxane PB fluorophores.

Figure 2:
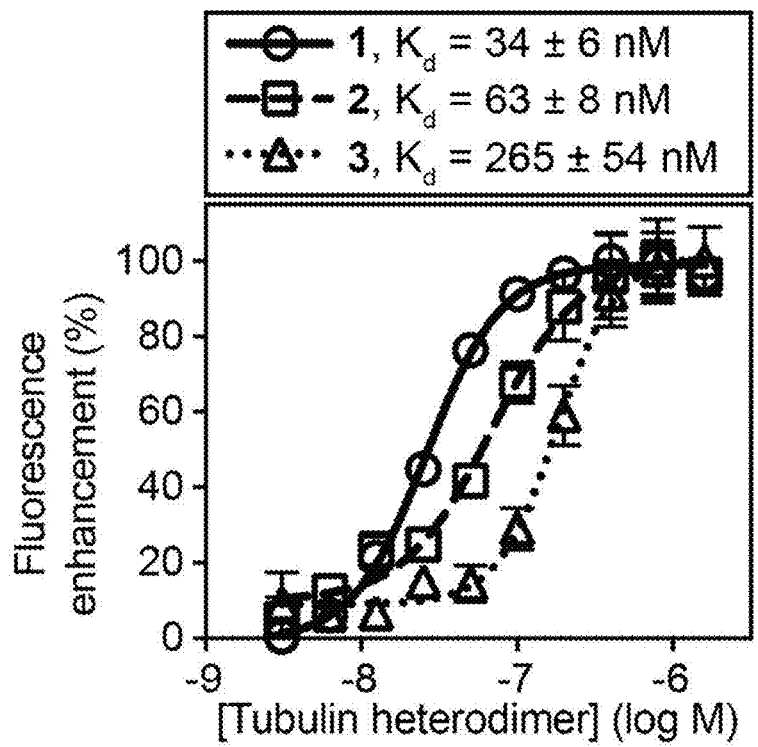
FIG. 2 includes a graph that shows the quantification of the affinities (Kd) of Compounds 1-3 for cross-linked microtubules by enhancement of fluorescence, where binding studies were conducted in aqueous GAB buffer (pH 6.5). PB was excited at 405 nm and emitted photons were collected at and above 450 nm.

Experiments were conducted to obtain the measured affinities of Compounds 1-3 for cross-linked microtubules from bovine brain using a fluorescence enhancement method (FIG. 2). FIG. 2 includes a graph that shows the quantification of the affinities (Kd) of Compounds 1-3 for cross-linked microtubules by enhancement of fluorescence, where binding studies were conducted in aqueous GAB buffer (pH 6.5). PB was excited at 405 nm and emitted photons were collected at and above 450 nm. Curve fitting of equilibrium binding curves yielded apparent Kd values of 34±6 nM for PB-Gly-Taxol (Compound 1), 63±8 nM for PB-β-Ala-Taxol (Compound 2), and 265±54 nM for PB-GABA-Taxol (Compound 3) in GAB buffer. Addition of excess paclitaxel (10 μM) blocked this fluorescence enhancement, demonstrating that Compounds 1-3 bind β-tubulin at the same site as paclitaxel (data not shown).

Figure 3:
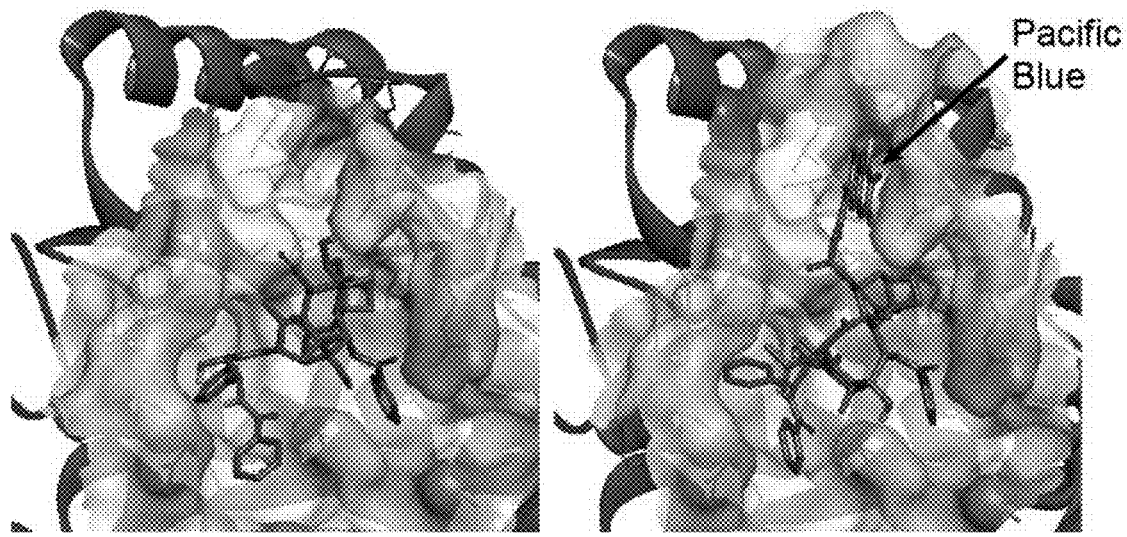
FIG. 3 shows a comparison of a published structure of paclitaxel bound to β-tubulin (PDB 3J6G, Panel A) with a model (Panel B) of β-tubulin docked to Compound 1. In Panel B, a docking pose of Compound 1 is shown where the side chain orientations are similar to those of paclitaxel in Panel A, and the PB moiety of Compound 1 engages a neighboring pocket on the protein surface.

The differences in the affinities of Compounds 1-3 were studied using Autodock vina to the paclitaxel-binding site from a recent Cryo-EM structure of β-tubulin bound to paclitaxel. These modeling studies suggested that linked fluorophores may favorably insert into a pocket near the paclitaxel-binding site (FIG. 3). As a result, using shorter linkers, such as n being 1 or glycine, may be advantageous. FIG. 3 shows a comparison of a published structure of paclitaxel bound to β-tubulin (PDB 3J6G, Panel A) with a model (Panel B) of β-tubulin docked to Compound 1. In Panel B, a docking pose of Compound 1 is shown where the side chain orientations are similar to those of paclitaxel in Panel A, and the PB moiety of Compound 1 engages a neighboring pocket on the protein surface.

Figure 4A:
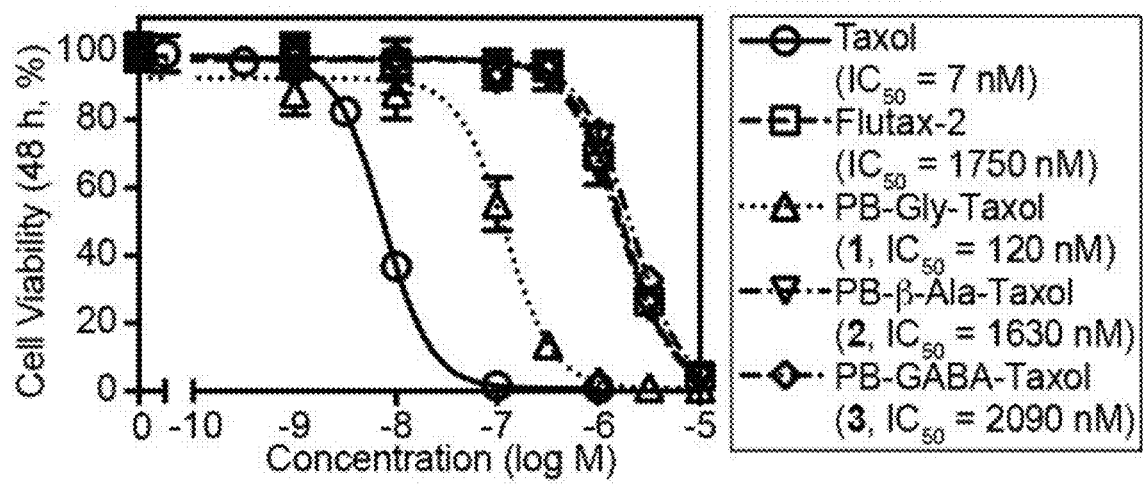
FIG. 4A shows a graph of an analysis of cytotoxicity for the compounds paclitaxel (Taxol®), Flutax-2®, Compound 1 (PB-Gly-Taxol), Compound 2 (PB-β-Ala-Taxol), and Compound 3 (PB-GABA-Taxol), where HeLa cells were treated with compounds in the absence of the efflux inhibitor verapamil (25 μM) for 48 hours (h) and cellular viability measured by flow cytometry.
Figure 4B:
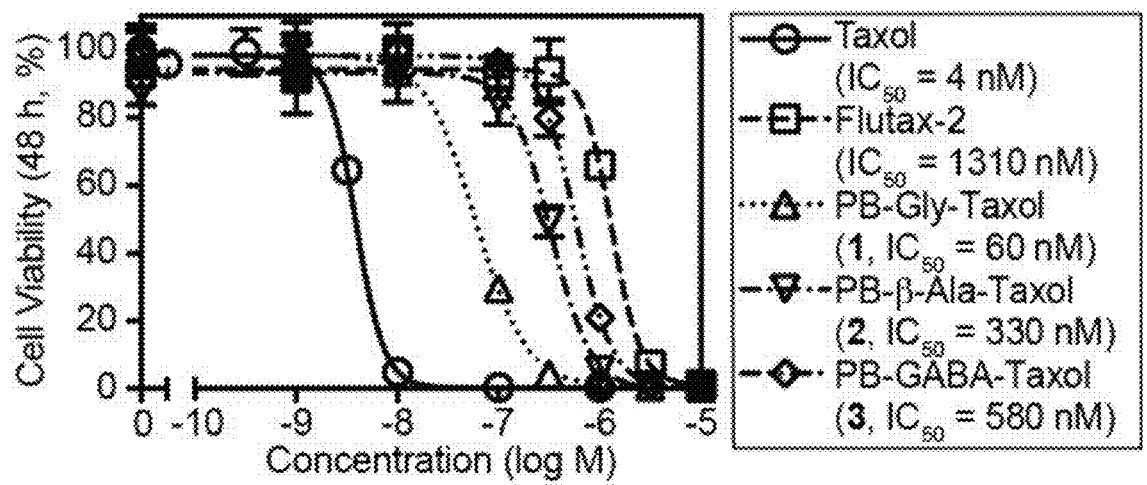
FIG. 4B shows a graph of an analysis of cytotoxicity for the compounds paclitaxel (Taxol®), Flutax-2®, Compound 1 (PB-Gly-Taxol), Compound 2 (PB-β-Ala-Taxol), and Compound 3 (PB-GABA-Taxol), where HeLa cells were treated with compounds in the presence of the efflux inhibitor verapamil (25 μM) for 48 h and cellular viability measured by flow cytometry.

The cytotoxicity of the taxane PB fluorophores towards HeLa cervical carcinoma cells (FIGS. 4A and 4B) was evaluated. These cell lines were treated for 48 h, cellular viability was analyzed by flow cytometry, and paclitaxel was used as a positive control. HCT-15 cells overexpress P-glycoprotein (P-gp, MDR1, ABCB1), and because paclitaxel is a substrate of this efflux transporter, the studies further measured cytotoxicity in the presence of the P-gp inhibitor verapamil (FIG. 4B). FIG. 4A shows a graph of an analysis of cytotoxicity for the compounds paclitaxel (Taxol®), Flutax-2®, Compound 1 (PB-Gly-Taxol), Compound 2 (PB-β-Taxol), and Compound 3 (PB-GABA-Taxol). HeLa cells were treated with compounds in the absence of verapamil (25 μM) for 48 h and cellular viability measured by flow cytometry. FIG. 4B shows a graph of an analysis of cytotoxicity for the compounds paclitaxel (Taxol®), Flutax-2®, Compound 1 (PB-Gly-Taxol), Compound 2 (PB-β-Taxol), and Compound 3 (PB-GABA-Taxol). HeLa cells were treated with compounds in the presence of verapamil (25 μM) for 48 h and cellular viability measured by flow cytometry.

Among the fluorescent probes, Compound 1 was uniquely toxic, with IC50=120 nM in the absence of verapamil, and IC50=60 nM in the presence of verapamil (25 μM) in HeLa cells. In HCT-15 cells, verapamil (25 μM) enhanced the toxicity of Compound 1 by 41-fold (from IC50=3.7 μM to IC50=90 nM). Control experiments confirmed that verapamil itself (IC50>75 μM at 48 h) did not contribute to these cytotoxic effects. HeLa cells express low levels of P-gp compared to HCT-15 cells, and this enhanced cytotoxicity mediated by verapamil indicates that Compounds 1-3 are highly efficient substrates of this drug efflux transporter. Flutax-2® is known to be a substrate of P-gp, but in HeLa cells treated with verapamil, Flutax-2® was the least cytotoxic (IC50=1310 nM), likely due to its higher polarity and associated lower cellular permeability or off-target effects.

Figure 5A:
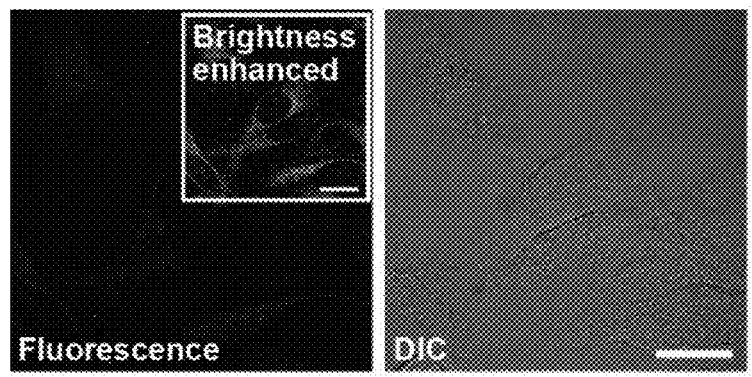
FIG. 5A includes an image from confocal laser scanning and DIC microscopy of living HeLa cells treated with Compound 1 (1 μM, 1 h) in the absence of verapamil, where the inset of FIG. 5A shows the brightness was enhanced to reveal weak fluorescence of 1 resulting from efflux. Scale bar=25 microns.
Figure 5B:
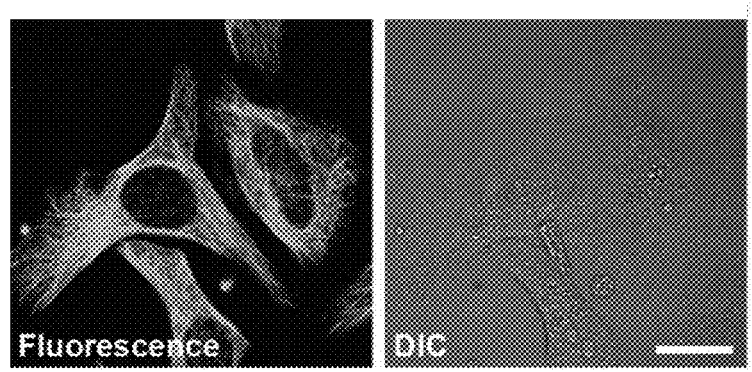
FIG. 5B includes an image from confocal laser scanning and DIC microscopy of living HeLa cells treated with Compound 1 (1 μM, 1 h) in the presence of verapamil (100 μM), where inhibition of efflux by verapamil results in binding of Compound 1 to microtubules. Scale bar=25 microns.
Figure 5C:
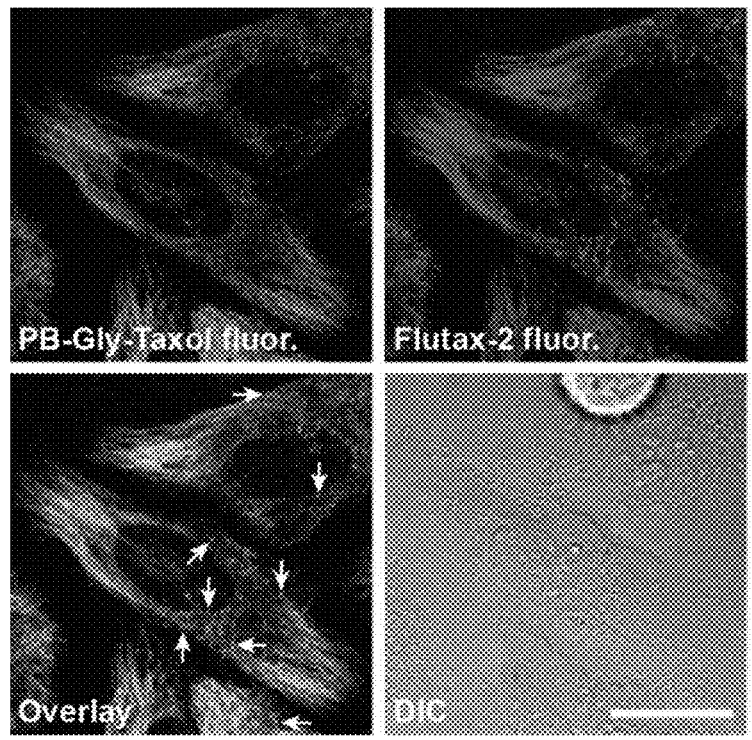
FIG. 5C shows where cells were further treated with Compound 1 (1 μM) verapamil (25 μM) and Flutax-2® (5 μM) for 1 hour to examine specificity. Arrows indicate unique punctate fluorescence of Flutax-2® that indicates its lower specificity for tubulin. Scale bar=25 microns.

To examine the subcellular distribution of Compound 1, HeLa cells were imaged by confocal laser scanning microscopy (FIGS. 5A, 5B, and 5C). After treatment of cells with 1 (1 μM, 1 h), cotreatment with verapamil dramatically enhanced cellular fluorescence in a dose dependent manner (FIGS. 5A, 5B, and 5C), revealing intricate networks of microtubules in living cells. FIG. 5A includes an image from confocal laser scanning and DIC microscopy of HeLa cells treated with Compound 1 (1 μM, 1 h) in the absence of verapamil (100 μM), where the inset of FIG. 5A shows the brightness was enhanced to reveal the weak fluorescence of Compound 1 resulting from efflux. FIG. 5B includes an image from confocal laser scanning and DIC microscopy of HeLa cells treated with Compound 1 (1 μM, 1 h) in the presence of verapamil (100 μM). FIG. 5C shows where cells were further treated with Compound 1 (1 μM) verapamil (25 μM) and Flutax-2® (5 μM) for 1 hour to examine specificity. Arrows indicate punctate fluorescence of Flutax-2® resulting from off-target effects. The distinct spectral profiles of PB and OG were used to further examine colocalization of Compound 1 and Flutax-2® (FIG. 5C). Whereas Compound 1 bound microtubules with very high specificity, Flutax-2® additionally conferred punctate fluorescence that did not co-localize with Compound 1 on microtubules.

Overexpression of P-gp frequently confers resistance to the antiproliferative effects of paclitaxel. Compound 1 is a substrate of P-gp, as shown by the study where transiently transfected PC-3 cells, which lack this transporter, with a plasmid (pHaMDR-EGFP) encoding P-gp fused to enhanced green fluorescent protein (EGFP). Unlike HeLa cells, imaging of PC-3 cells treated with Compound 1 (1 μM) revealed strong blue fluorescence in the absence of verapamil (data not shown). However, in cells expressing green fluorescent P-gp-EGFP, decreased blue fluorescence was observed, dependent on the level of P-gp-EGFP expression, indicating that Compound 1 is a potent substrate of this transporter. Treatment with verapamil reversed this effect by blocking P-gp to prevent efflux of Compound 1.

Figure 6A:
FIG. 6A shows an image from confocal laser scanning and DIC microscopy of living HCT-15 cells treated with the P-gp substrate rhodamine 123 (1 μM) with the vehicle only (left Fluor. and DIC panels) and with the P-gp inhibitor verapamil (25 μM, 1 h, right Fluor. and DIC panels, resulting in enhanced cellular fluorescence).
Figure 6B:
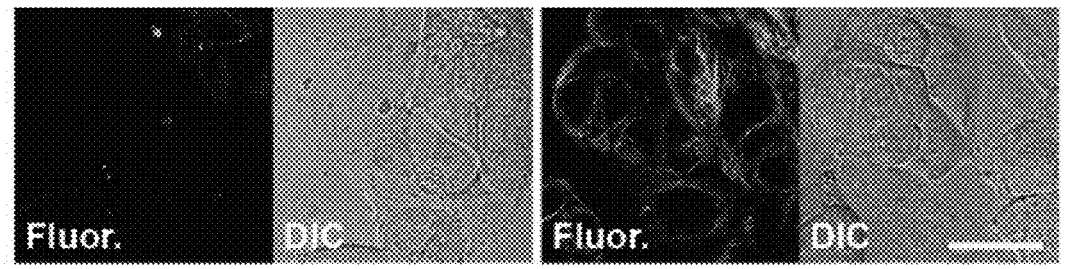
FIG. 6B shows an image from confocal laser scanning and DIC microscopy of living HCT-15 cells treated with the P-gp substrate Compound 1 (1 μM) with the vehicle only (left Fluor. and DIC panels), and with verapamil (25 μM, 1 h, right Fluor. and DIC panels, resulting in enhanced cellular fluorescence). Scale bar=25 microns.
Figure 6C:
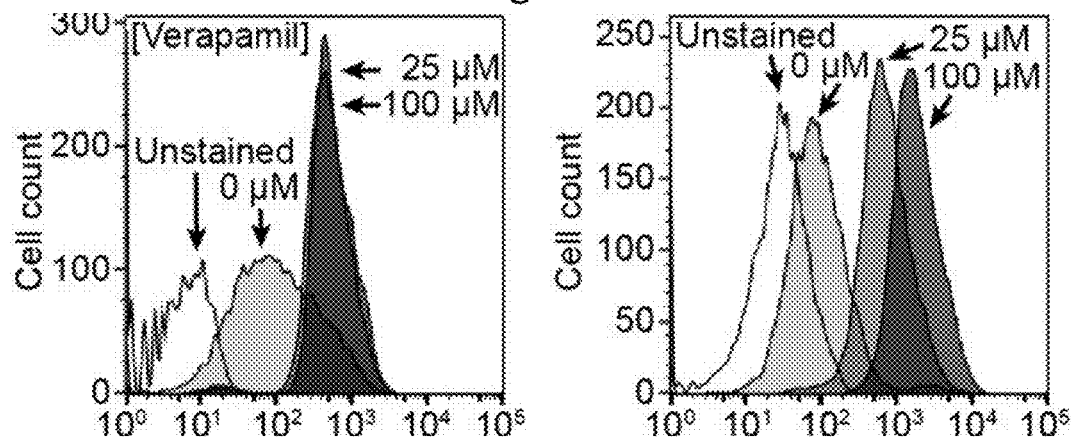
FIG. 6C shows data from an analysis of living HCT-15 cells treated with rhodamine 123 (1 μM) (left panels) or Compound 1 (1 μM) (right panels) by flow cytometry. Concentrations of added verapamil are shown.
Figure 6D:
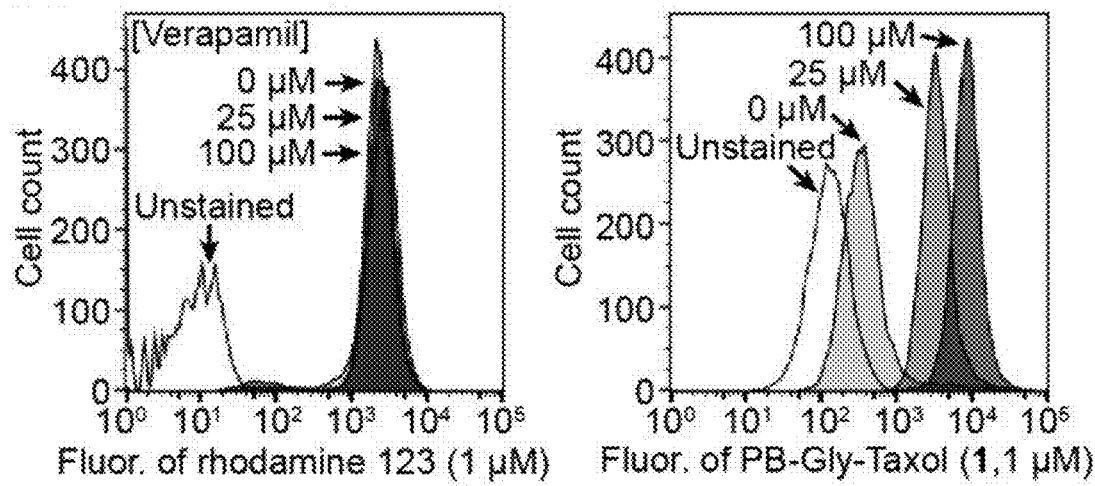
FIG. 6D shows data from an analysis of living HeLa cells treated with rhodamine 123 (1 μM) (left panels) or Compound 1 (1 μM) (right panels) by flow cytometry. Concentrations of added verapamil are shown.

Studies were conducted to investigate the efflux of Compound 1 in HCT-15 cells that express high levels of P-gp. Compound 1 was compared with rhodamine 123 (Rho123), a common P-gp substrate that accumulates in mitochondria. As shown in FIGS. 6A-6D, cells were analyzed after treatment with Compound 1 (1 μM), Rho123 (1 μM), and verapamil (0, 25, 100 μM) by confocal microscopy and flow cytometry. FIG. 6A shows an image from confocal laser scanning and DIC microscopy of HCT-15 cells treated with the P-gp substrates rhodamine 123 (1 μM) with the vehicle only, left 2 panels, and with verapamil (25 μM, 1 h). FIG. 6B shows an image from confocal laser scanning and DIC microscopy of HCT-15 cells treated with the P-gp substrates Compound 1 (1 μM) with the vehicle only, left 2 panels, and with verapamil (25 μM, 1 hr). FIG. 6C shows data from an analysis of HCT-15 cells treated with rhodamine 123 (1 μM) (left panels) or Compound 1 (1 μM) (right panels) by flow cytometry, were concentrations of added verapamil are shown. FIG. 6D shows data from an analysis of HeLa cells treated with rhodamine 123 (1 μM) (left panels) or Compound 1 (1 μM) (right panels) by flow cytometry, where concentrations of added verapamil are shown. Whereas the fluorescence of Rho123 increased by only 3-fold in the presence of verapamil (at 25 or 100 μM), the fluorescence of Compound 1 increased by 7-fold at 25 μM and 15-fold at 100 μM verapamil. Moreover, in HeLa cells, Compound 1 could detect low levels of P-gp activity in HeLa cells that were undetectable by Rho123 (FIG. 6D), enhancing fluorescence by 10-fold at 25 μM verapamil and 23-fold at 100 μM verapamil, indicating that Compound 1 can be used as a uniquely sensitive sensor of this efflux transporter.

In contrast to Flutax-2®, which is only weakly cytotoxic, and exhibits relatively low cellular permeability due to the high polarity of the appended OG fluorophore, the more drug-like Compound 1 substantially recapitulates aspects of the cytotoxic, tubulin-binding, and P-gp-mediated efflux activity of the parent anticancer drug. Because PB can be efficiently detected and analyzed by confocal microscopy and flow cytometry, this probe offers a new tool for studies of the paradoxical anticancer effects of paclitaxel. Thus, the taxane PB fluorophores are superior to Flutax-2®. As such, Compounds 1-3 can be used to study the proliferation rate paradox associated with the parent drug.

Figure 7:
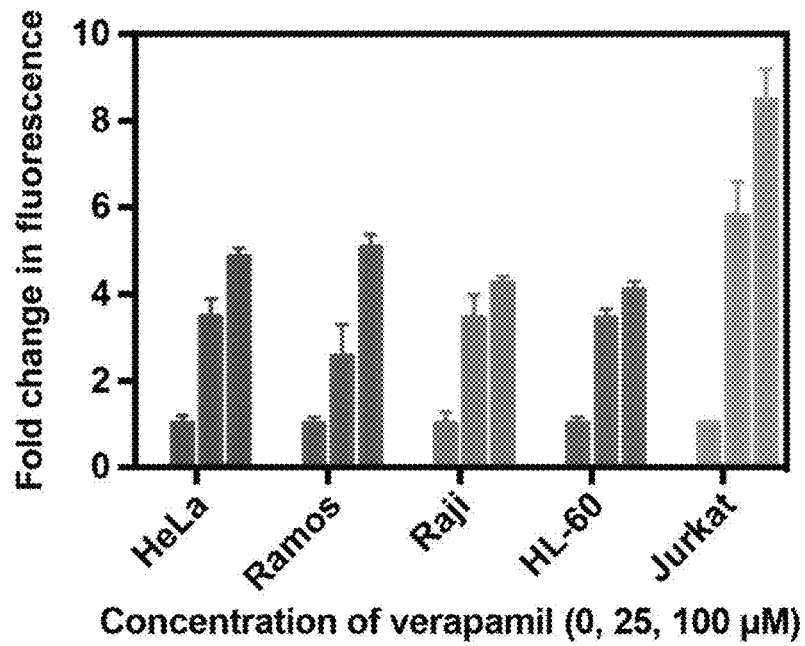
FIG. 7 shows a graph of data for the uptake of Compound 1 into living HeLa, Ramos, Raji, HL-60, and Jurkat cell lines by flow cytometry, illustrating increased uptake with addition of increasing concentrations of verapamil.

The uptake of Compound 1 (PB-Gly-Taxol, at 1 μM, 1 h, 200,000 cells/200 μL) by different cell lines was studied and quantified by using flow cytometry. The study was done with different concentrations of verapamil or no verapamil such as, 0 µM, 25 µM, 100 µM, for the data bars going from left to right for each cell type. As shown in FIG. 7, the inclusion of verapamil increased the uptake. FIG. 7 shows a graph of data for the uptake of Compound 1 into the HeLa, Ramos, Raji, HL-60, and Jurkat cell lines, and the update was increased by adding increasing amounts of verapamil. These experiments demonstrate the high sensitivity of Compound 1 (PB-Gly-Taxol) for detection of P-gp in a wide variety of cell lines including both adherent and suspension cells.

Additional information regarding the synthesis and characterization of Compounds 1-3, and relevant data thereof is included in the provisional application that is incorporated herein by specific reference in its entirety.

Figure 8A:
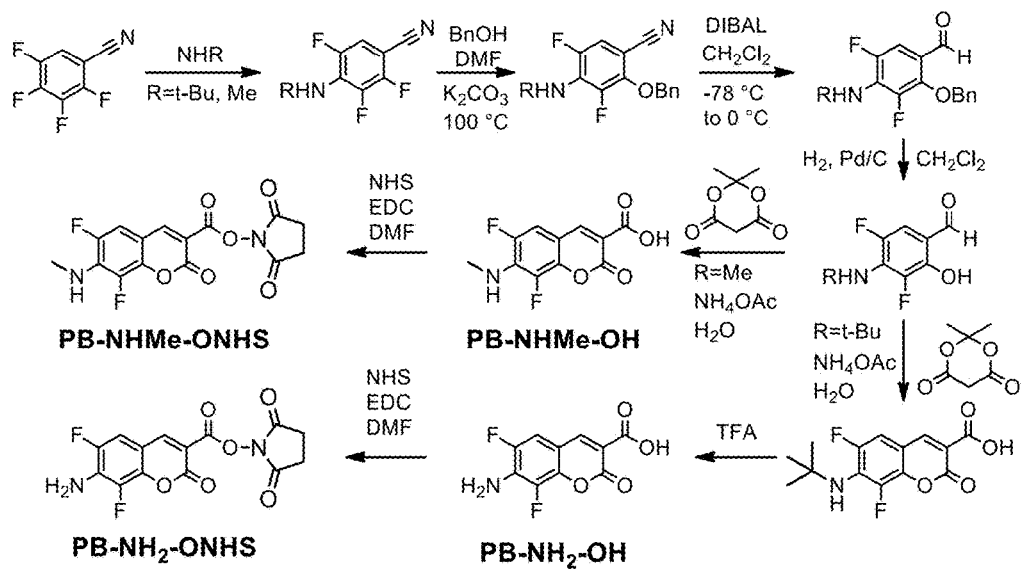
FIG. 8A shows reaction Scheme 2 to prepare amino derivatives of Pacific Blue that can be used to prepare other taxane PB fluorophores.
Figure 8B:
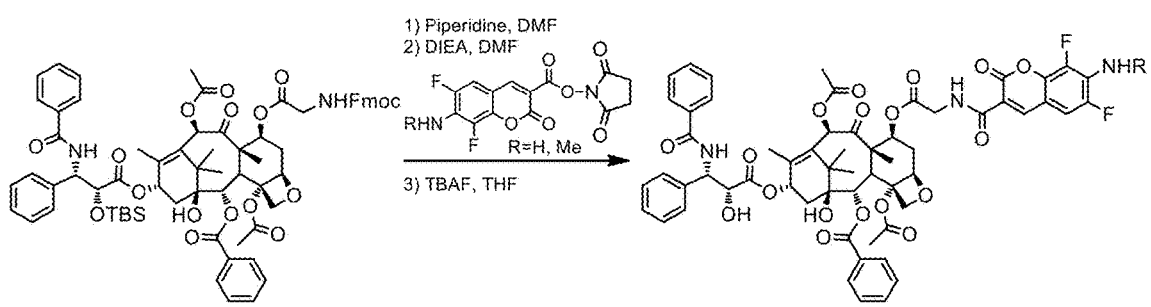
FIG. 8B shows reaction Scheme 3 to prepare representative taxane PB-amine (PB-$NH_2$ and PB-NHMe) fluorophores.

While the previously discussed reaction schemes and data included the compounds under Formula 1 where the R group is the oxygen anion or hydroxide (e.g. forming the phenoxide), now the compounds that fall under Formula 2 with the R1 and R2 group are described. FIG. 8A shows reaction Scheme 2 that is performed in order to prepare alternative coumarin analogues of Pacific Blue that can be used to prepare the compounds under Formula 2. It should be recognized that the reaction in Scheme 2 may be modulated so that the R group can vary to be any of the substituents recited herein. Then, FIG. 8B shows the reaction Scheme 3 that is performed to prepare the taxane (e.g., paclitaxel) into the taxane PB fluorophores under Formula 2. Also, it should be recognized that any taxane may be prepared as shown to be the reagent in order to prepare a wide variety of taxane PB fluorophores.

Figure 9:
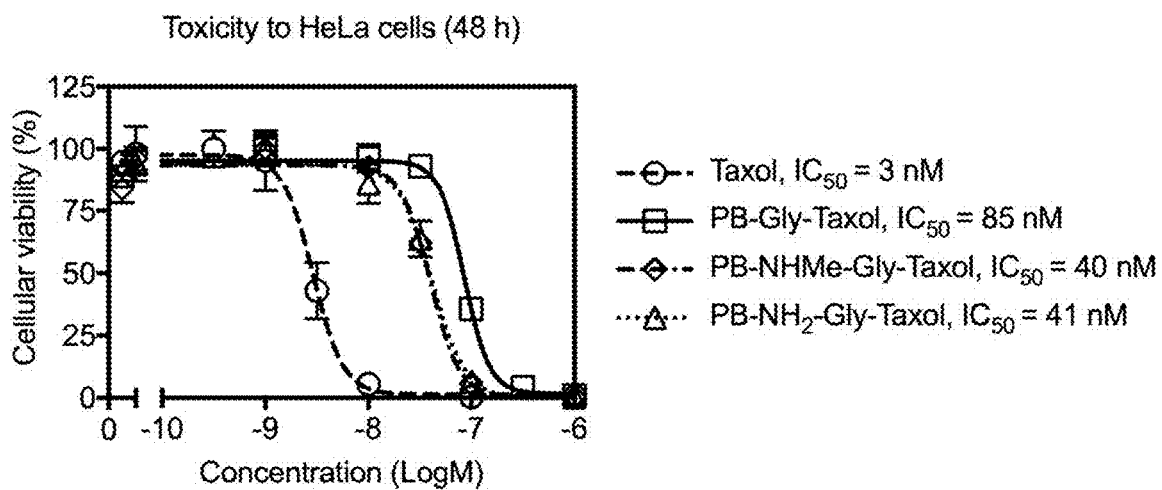
FIG. 9 shows a graphical analysis of the toxicity of paclitaxel (Taxol®), PB-Gly-Taxol (Compound 1), PB-NHMe-Gly-Taxol (Compound 21), and PB-NH$_2$-Gly-Taxol (Compound 22).

An experiment was conducted to determine the toxicity of paclitaxel (Taxol®), PB-Gly-Taxol (Compound 1), PB-NHMe-Gly-Taxol (Compound 21), and PB-NH2-Gly-Taxol (Compound 22) in HeLa cells. FIG. 9 shows a graph for the toxicity of paclitaxel (Taxol®), PB-Gly-Taxol (Compound 1), PB-NHMe-Gly-Taxol (Compound 21), and PB-NH2-Gly-Taxol (Compound 22), which shows the cellular viability (percentage) versus concentration. The IC50s were also determined. The data shows that PB-Gly-Taxol (Compound 1) is less toxic than PB-NHMe-Gly-Taxol (Compound 21), but these specific compounds are less toxic than paclitaxel. As such, PB-NHMe-Gly-Taxol (Compound 21) and PB-NH2-Gly-Taxol (Compound 22) may exhibit beneficial properties as anticancer agents compared with PB-Gly-Taxol (Compound 1). Also, because PB-NHMe-Gly-Taxol (Compound 21) and PB-NH2-Gly-Taxol (Compound 22) show a unique pattern of subcellular accumulation in the endoplasmic reticulum these compounds may be used as a probe for cytotoxic effects of paclitaxel targets in the endoplasmic reticulum. Because these and related compounds associate with internal membranes of the endoplasmic reticulum, they may further exhibit beneficial properties as therapeutic agents by avoiding efflux mediated by P-gp, a transporter found at the cellular plasma membrane, and yet still allow exchange between the endoplasmic reticulum and microtubules found throughout cells to manifest toxicity.

Figure 10A:
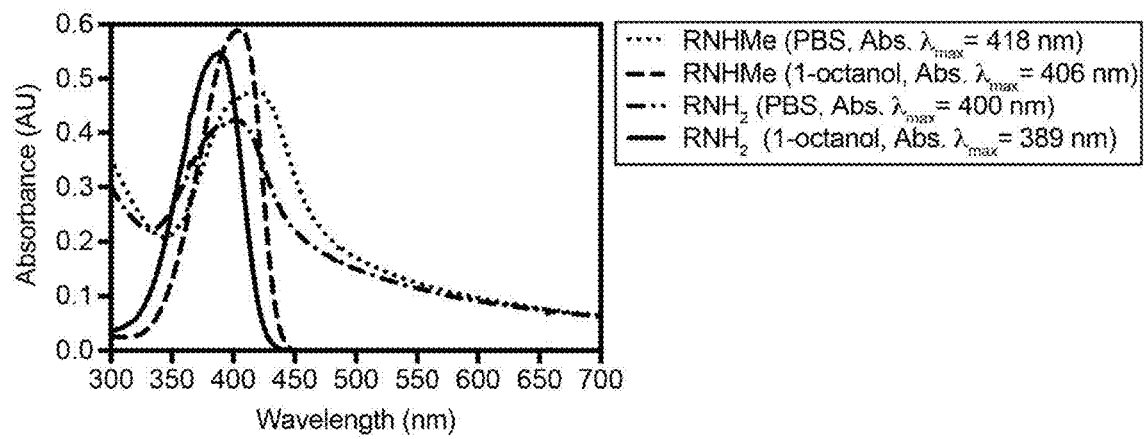
FIG. 10A show a graph of absorbance for PB-NHMe-Gly-Taxol and PB-NH$_2$-Gly-Taxol in phosphate buffered saline (PBS, pH 7.4) and 1-octanol (as a mimic of cellular membranes).

Additionally, the absorbance spectra were determined for 30 µM PB-NHMe-Gly-Taxol (Compound 21, RNHMe) and PB-NH$_2$-Gly-Taxol (Compound 22, RNH2) in PBS and 1-octanol. FIG. 10A shows the absorbance spectra for PB-NHMe-Gly-Taxol (Compound 21, RNHMe) and PB-NH2-Gly-Taxol (Compound 22, RNH2) in PBS and 1-octanol along with the maximum absorbance wavelength. It should be recognized that for Formula 1, Compound 21 has R being —NH—CH$_3$ and Compound 22 has R being —NH$_2$.

Figure 10B:
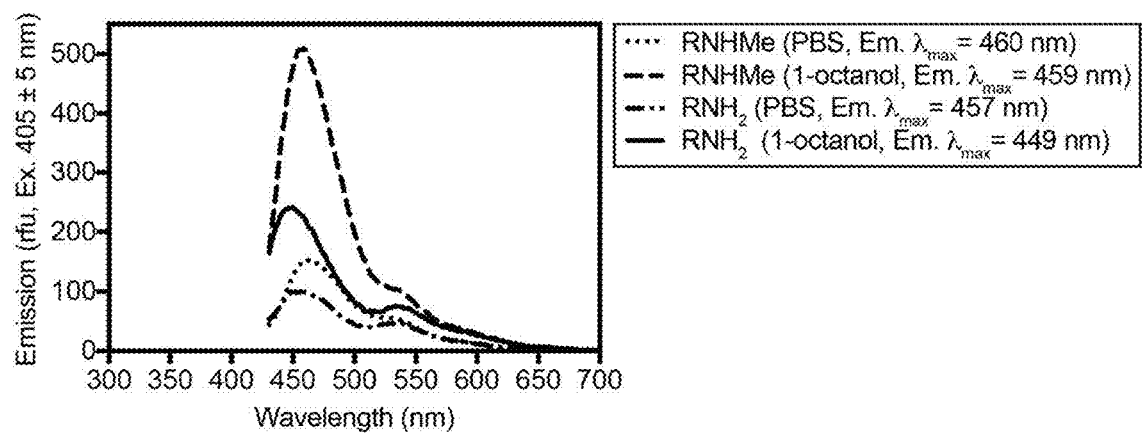
FIG. 10B show a graph of emission for PB-NHMe-Gly-Taxol and PB-NH$_2$-Gly-Taxol in phosphate buffered saline (PBS, pH 7.4) and 1-octanol (as a mimic of cellular membranes).

Also, the emission spectra were determined for 50 nM PB-NHMe-Gly-Taxol (Compound 21, RNHMe) and PB-NH$_2$-Gly-Taxol (Compound 22, RNH$_2$) in PBS and 1-octanol. FIG. 10B shows the emission spectra for PB-NHMe-Gly-Taxol (Compound 21, RNHMe) and PB-NH$_2$-Gly-Taxol (Compound 22, RNH$_2$) in PBS and 1-octanol along with the maximum emission wavelength.

Figure 11:
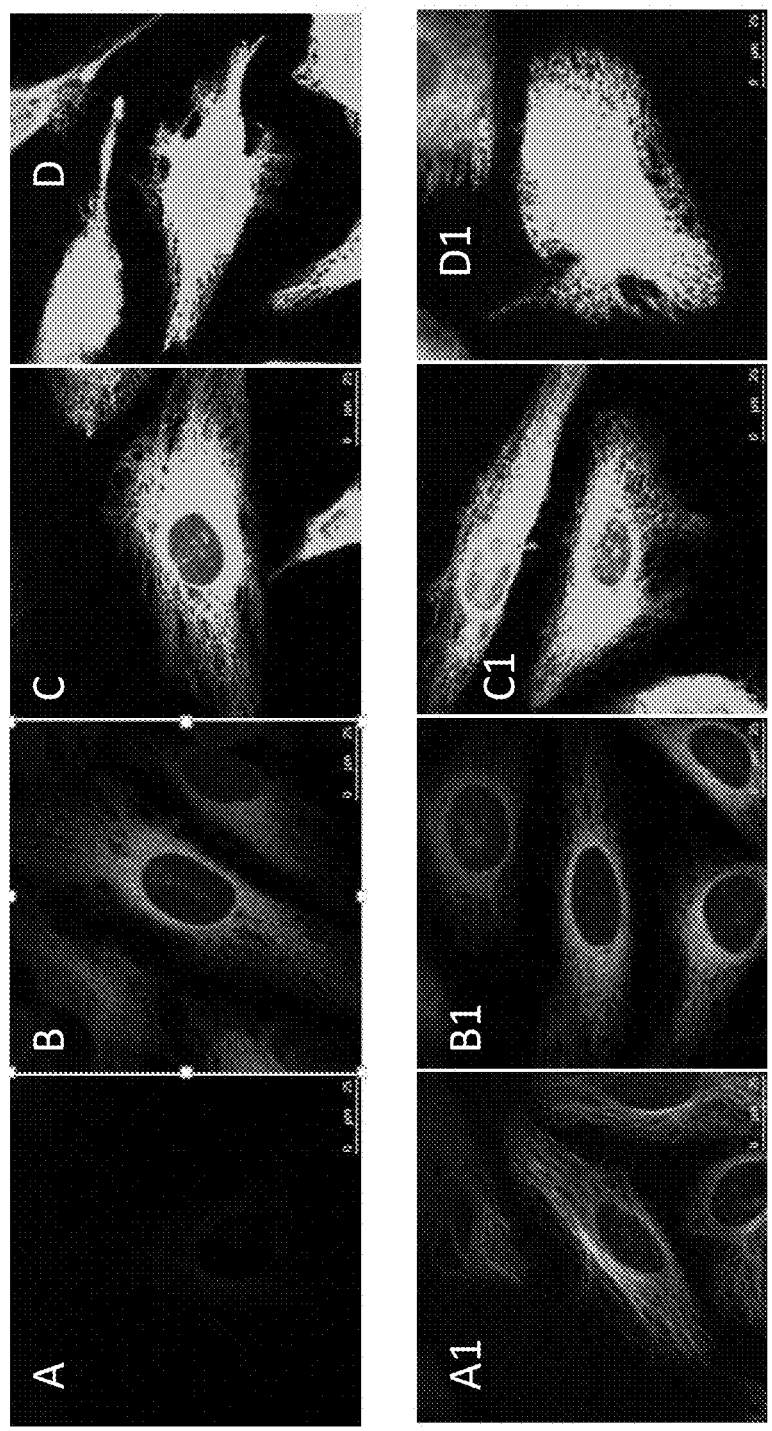
FIG. 11 shows images of a P-glycoprotein response to PB-Gly-Taxol (1 Panels A and A1) and PB-NHMe-Gly-Taxol (Panels B and B1 (10 nM), C and C1 (100 nM) and D and D1 (1 µM) in living HeLa cells. In panels A-D vehicle (DMSO, 0.1%) only was added as a control. In panels A1-D1, verapamil (25 µM) was added to inhibit P-gp. Unlike PB-Gly-Taxol, PB-NHMe-Gly-Taxol and PB-NH$_2$-Gly-Taxol (data not shown) do not undergo efficient efflux by P-gp.

Experiments were conducted to determine whether or not PB-NHMe-Gly-Taxol (Compound 21) is a substrate of P-glycoprotein in HeLa cells. Confocal microscopy revealed that PB-NHMe-Gly-Taxol and PB-NH2-Gly-Taxol are not substrates of P-glycoprotein and accumulate in the endoplasmic reticulum of live cells, as shown in FIG. 11. The low fluorescence of these compounds in aqueous solution compared to membrane mimics such as 1-octanol (FIG. 10) may limit visualization of microtubules in cells with these compounds. The observation that these compounds retain high cytotoxicity (suggesting interaction with microtubules that cannot be readily visualized) and avoid efflux by P-gp, while accumulating in the endoplasmic reticulum, suggest that they may exhibit unique and beneficial therapeutic effects compared with paclitaxel. FIG. 11 shows images of a P-glycoprotein response to PB-Gly-Taxol and PB-NHMe-Gly-Taxol, with or without verapamil. The experiment was conducted by 1 hour incubation with HeLa cells, followed by a wash and then imaging using a 25% laser power with excitation at 405 nm and emission at 425-500 nm. The top left Panel A shows 1 µM PB-Gly-Taxol (Compound 1), and Panel A1 is the same as Panel A plus 25 µM verapamil. Panel B shows 10 nM PB-NHMe-Gly-Taxol, and Panel B1 is the same as Panel B plus 25 µM verapamil. Panel C shows 100 nM PB-NHMe-Gly-Taxol, and Panel C1 is the same as Panel C plus 25 µM verapamil. Panel D shows 1 µM PB-NHMe-Gly-Taxol, and Panel D1 is the same as Panel D plus 25 µM verapamil.

Figure 12:
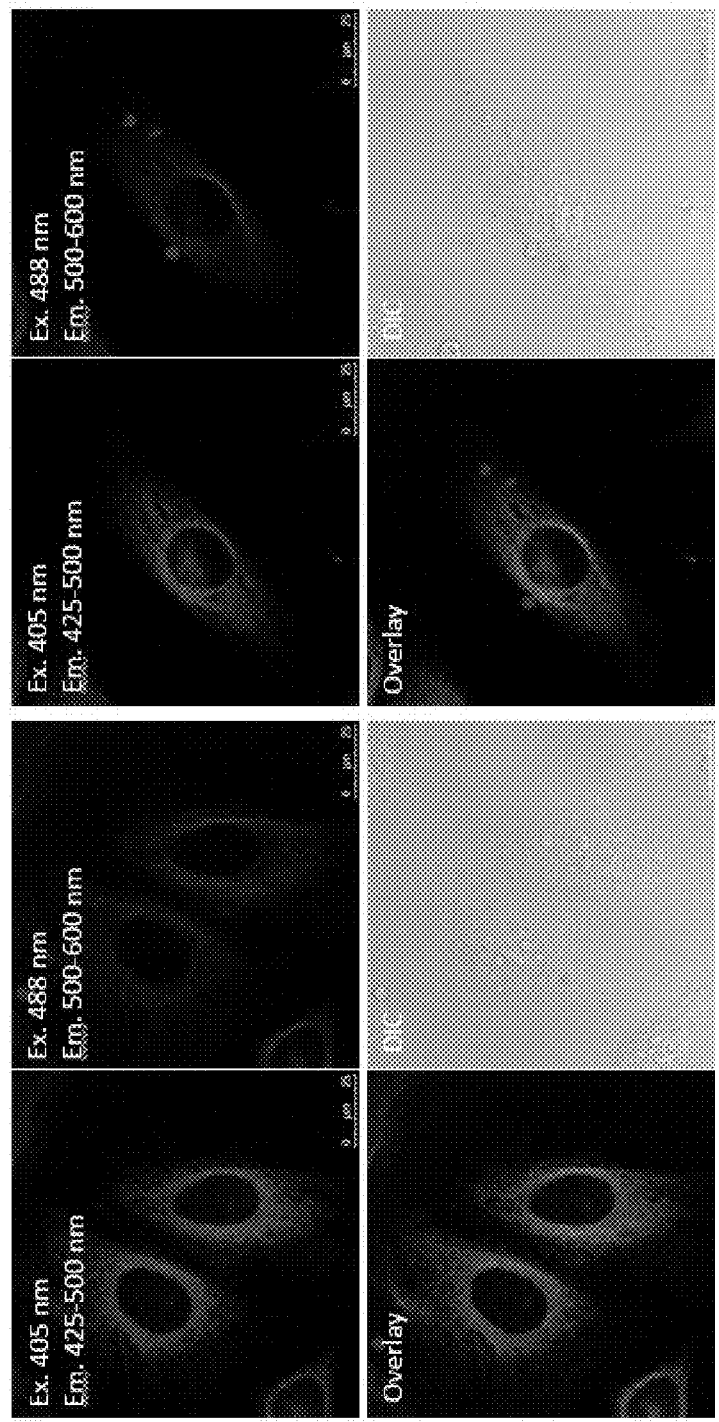
FIG. 12 shows PB-NHMe-Gly-Taxol (Compound 21) does not visibly colocalize with Flutax-2® on microtubules in live HeLa cells but rather extensively associates with internal membranes of the endoplasmic reticulum. Differences in photophysical properties of these fluorophores may prevent visualization of binding of PB-NHMe-Gly-Taxol (Compound 21) to microtubules in living cells.

Experiments were conducted to determine whether or not PB-NHMe-Gly-Taxol (Compound 21) can colocalize with Flutax-2® on microtubules in live cells by confocal microscopy. Confocal microscopy indicated that PB-NHMe-Gly-Taxol (Compound 21) does not appear to colocalize with Flutax-2® on microtubules in live HeLa cells but rather has a unique pattern of subcellular localization that could benefit therapeutic applications by enhancing the residence time in cancer cells. The colocalization assay included 10 nM of PB-NHMe-Gly-Taxol (Compound 21) with 5 µM Flutax-2® and 25 verapamil in HeLa cells for 1 hour. FIG. 12 shows different images in the panels for different excitation wavelengths and emission wavelengths, as well as overlays and the DIC microscopy images. FIG. 12 shows PB-NHMe-Gly-Taxol (Compound 21) does not colocalize with Flutax-2® on microtubules in live HeLa cells.

Figure 13:
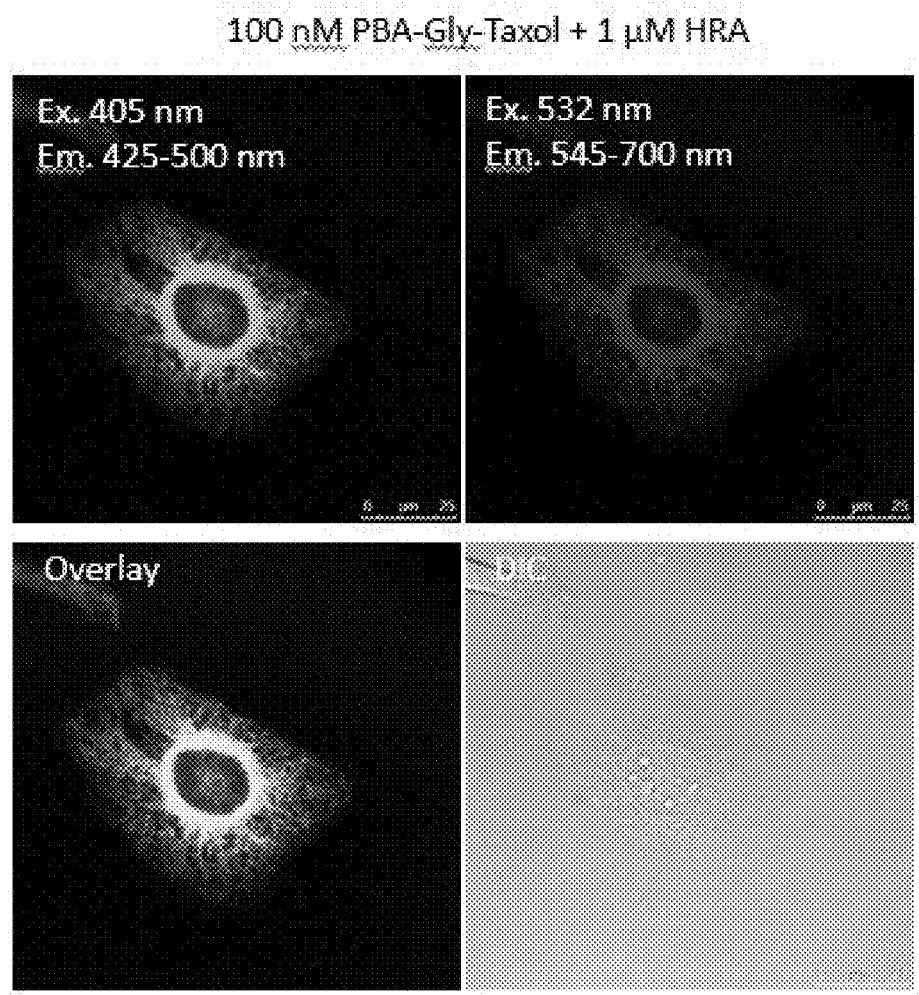
FIG. 13 shows that PB-NHMe-Gly-Taxol (Compound 21) specifically colocalizes with the fluorescent probe HRA (hexyl resorufamine) in membranes of the endoplasmic reticulum of living HeLa cells.

Studies were conducted to determine if PB-NHMe-Gly-Taxol (Compound 21) interacted with the endoplasmic reticulum, and was compared to red fluorescent endoplasmic reticulum probe HRA (hexyl resorufamine) in live cells using fluorescent microscopy. The colocalization assay was conducted with 100 nM PB-NHMe-Gly-Taxol with 1 µM HRA in HeLa for 1 h. FIG. 13 shows different images with different wavelengths and the overlay thereof as well as the DIC image. This shows that PB-NHMe-Gly-Taxol colocalizes with the red fluorescent endoplasmic reticulum probe HRA in live HeLa cells.

Figure 14:
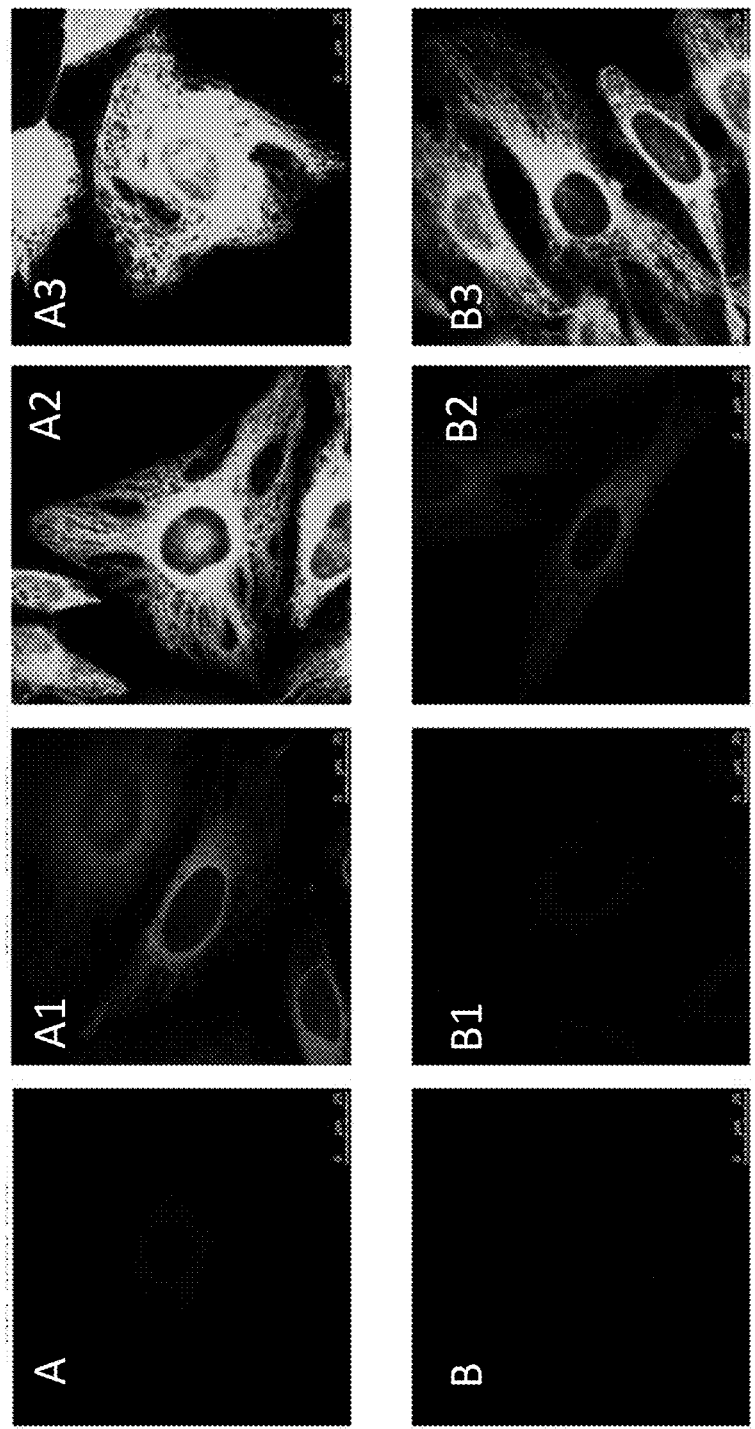
FIG. 14 shows confocal microscopy images of living HeLa cells treated with PB-NHMe-Gly-Taxol (Compound 21, top panels) and ER Tracker Blue-White DPX (bottom panels). Concentrations of probes (left to right: 1 nM, 10 nM, 100 nM, 1 µM). PB-NHMe-Gly-Taxol shows greater potency in its accumulation in ER membranes.

Studies were conducted to determine whether or not PB-NHMe-Gly-Taxol (Compound 21) is potent as an endoplasmic reticulum probe. The studies compared the potency as an endoplasmic reticulum probe with commercial ER probe ER Tracker Blue-White DPX. The amounts of PB-NHMe-Gly-Taxol (Compound 21) and ER Tracker Blue-White DPX were increased by Panels A through A3 showing PB-NHMe-Gly-Taxol (Compound 21) and Panels B through B3 showing ER Tracker Blue-White DPX. Panels A and B used 1 nM of the compounds, Panels A1 and B1 used 10 nM of the compounds, Panels A2 and B2 used 100 nM of the compounds, and Panels A3 and B3 used 1 µM of the compounds. FIG. 14 shows confocal microscopy images of endothelium reticulum interaction at increasing concentrations for PB-NHMe-Gly-Taxol (Compound 21, A-A3) and ER Tracker Blue-White DPX (B-B3). Accordingly, PB-NHMe-Gly-Taxol (Compound 21) is more potent as an endothelium reticulum probe compared to ER Tracker Blue-White DPX. These results demonstrate that modification of taxoids with coumarin-derived fluorophores can provide a novel method to reduce the sensitivity of taxoids to efflux by P-glycoprotein by causing accumulation in the endoplasmic reticulum while retaining substantial toxicity against cancer cells.

Additionally, studies were done that show that it is surprising and unexpected that the compounds described herein, such as Compound 2 (PB-β-Ala-Taxol) can bind to microtubules better than when paclitaxel is coupled to a different fluorophore, such as when forming iPr-Rhodol-β-Ala-Taxol. As such, small changes to the fluorophore core structure can prevent the paclitaxel fluorescent derivative from performing or acting the same as paclitaxel, and such small changes can reduce binding of fluorescent taxanes to microtubules. As such, Compound 2 (PB-β-Ala-Taxol) was compared to iPr-Rhodol-β-Ala-Taxol with HeLa cells transfected with mCherry-tubulin. In contrast to PB-β-Ala-Taxol, the iPr-Rhodol-β-Ala-Taxol does not bind extensively to microtubules, but rather appears to accumulate predominantly in the endoplasmic reticulum of living HeLa cells, in this case without engendering substantial cytotoxicity, unlike the more toxic coumarin-linked taxoids PB-NHMe-Taxol and PB-NH$_2$-Taxol that also accumulate in this organelle.

about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms

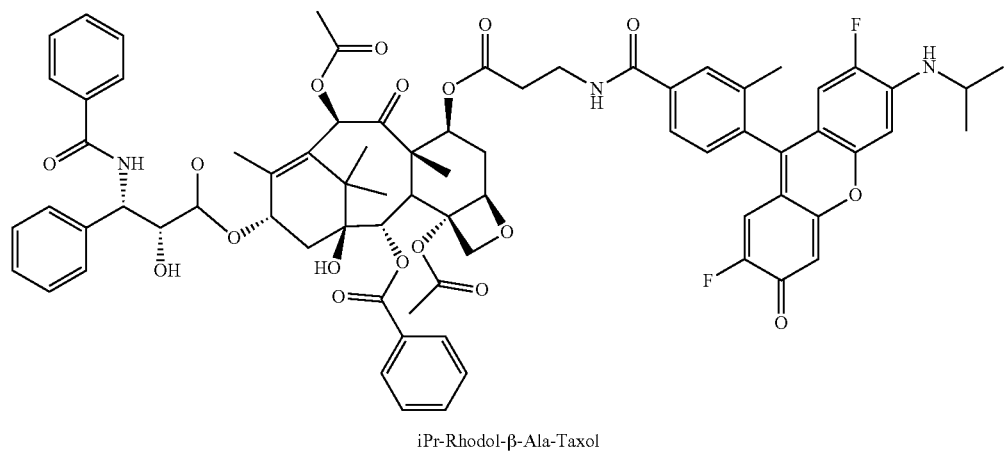

iPr-Rhodol-β-Ala-Taxol

Definitions

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenyl cyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

All other chemistry terms are defined as known in the art.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above.

Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A compound comprising:
   a structure of Formula 9, salt, stereoisomer, tautomer, polymorph, or solvate thereof;

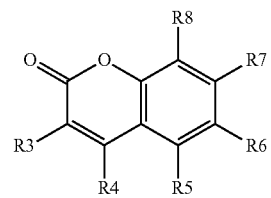

Formula 9 wherein:
R3, R4, R5, R6, R7, and/or R8 are independently any substituent provided that at least one of R3, R4, R5, R6, R7, and/or R8 is a taxane coupled to a linker, wherein the linker is coupled to Formula 9.

2. The compound of claim 1, comprising:
   a fluorescent taxane derivative having a structure of Formula 1, salt, stereoisomer, tautomer, polymorph, or solvate thereof;

Formula 1

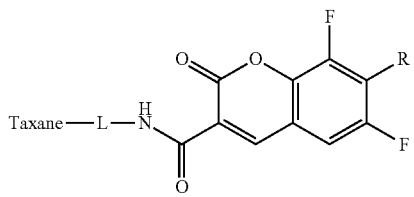

wherein:
L, L-NH, or L-NH—C=O is the linker;
R is selected from:
(a) —NH₂, —NH-alkyl, —N(alkyl)₂, —NH₂—R1, —N(R1)₂ or NR1R2, or combination thereof;
(b) —C(O)R1a, —C(O)CH(NR1bR1c)R1a, —C(O)CH(N(R1c)C(O)R1b)R1a, —C(O)CH(N(R1c)C(O)OR1b)R1a, —C(O)CH(N(R1c)C(O)NR1bR1d)R1a, —C(O)OR1a, —C(O)NR1bR1c, —C(NR1a)NR1bR1c, —P(O)(OR1a)R1d, —CH2P(O)(OR1a)R1d, —S(O)R1a, —S(O)2R1a, —S(O)NR1bR1c, or —S(O)2NR1bR1c;
(c) $C_1$-$C_{24}$ alkyl, $C_2$-$C_{24}$ alkenyl, $C_2$-$C_{24}$ alkynyl, $C_3$-$C_{20}$ cycloalkyl, $C_5$-$C_{20}$ aryl, $C_5$-$C_{20}$ polyaryl, $C_6$-$C_{24}$ alkaryl, $C_6$-$C_{24}$ aralkyl, heteroaryl, heterocyclyl, hydrogen, halo, oxygen anion, hydroxy anion, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl, $C_6$-$C_{20}$ arylcarbonyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino, or combinations thereof; and
(d) combinations thereof;
wherein the R group is optionally substituted by a substituent Q, which substituent Q is defined as R; and
wherein R1, R2, R1a, R1b, R1c, or R1d are each independently as defined for R or independently hydrogen.
3. The compound of claim 2, wherein the linker is selected from:
$C_1$-$C_{24}$ alkyl, $C_2$-$C_{24}$ alkenyl, $C_2$-$C_{24}$ alkynyl, $C_3$-$C_{20}$ cycloalkyl, $C_5$-$C_{20}$ aryl, $C_5$-$C_{20}$ polyaryl, $C_6$-$C_{24}$ alkaryl, $C_6$-$C_{24}$ aralkyl, heteroaryl, heterocyclyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl, $C_6$-$C_{20}$ arylcarbonyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, amino, amino acid, essential amino acid, L-amino acid, D-amino acid, non-essential amino acid, glycine, beta-alanine, gamma-aminobutyric acid (GABA), mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, or combinations thereof; or

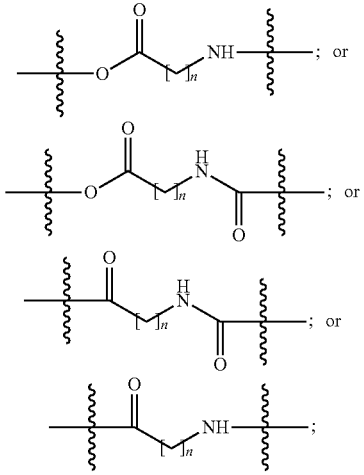

wherein n is an integer.
4. The compound of claim 3, wherein the linker is selected from glycine, beta-alanine, gamma-aminobutyric acid (GABA).
5. The compound of claim 3, wherein the linker is glycine.
6. The compound of claim 3, wherein:
R is selected from —O⁻, —OH, —NH₂, —NH-alkyl, —N(alkyl)₂, —NH₂—R1, —N(R1)₂ or —NR1R2;
R1 is $C_1$-$C_{24}$ alkyl; and
R2 is hydrogen or $C_1$-$C_{24}$ alkyl.
7. The compound of claim 6, wherein the R1 or alkyl is methyl and R2 is hydrogen.
8. The compound of claim 6, wherein R is selected from —O⁻, —OH, —NH-methyl.
9. The compound of claim 6, wherein the linker is selected from glycine, beta-alanine, gamma-aminobutyric acid (GABA).
10. The compound of claim 4, wherein the fluorescent taxane derivative is selected from Formula 3, Formula 4, or Formula 5 or salt, stereoisomer, tautomer, polymorph, or solvate thereof:

Formula 3

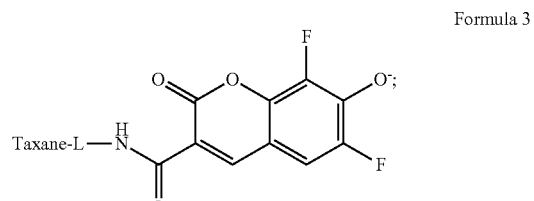

Formula 4

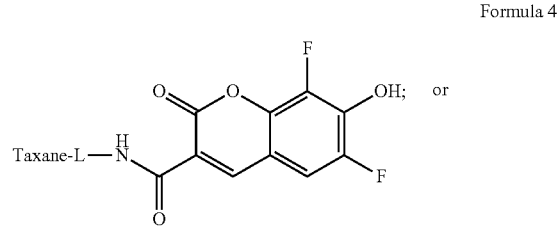

or

Formula 5

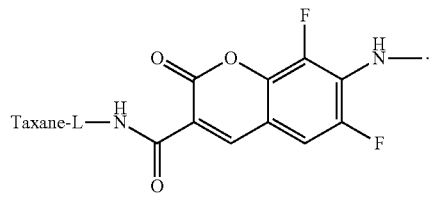

11. The compound of claim 2, wherein the fluorescent taxane derivative is selected from Formula 6, Formula 7, or Formula 8 or salt, stereoisomer, tautomer, polymorph, or solvate thereof:

Formula 6

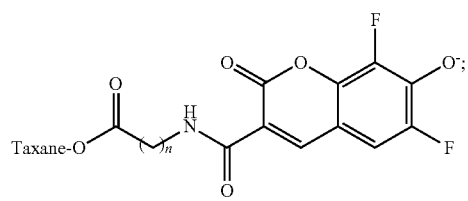

Formula 7

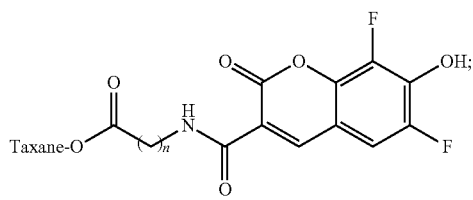

Formula 8

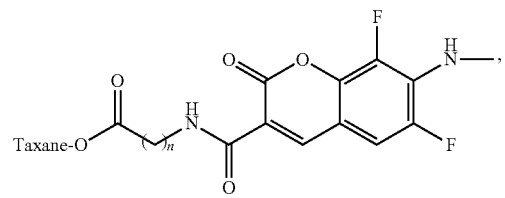

wherein n is an integer.

12. The compound of claim 2, wherein the taxane is selected from:

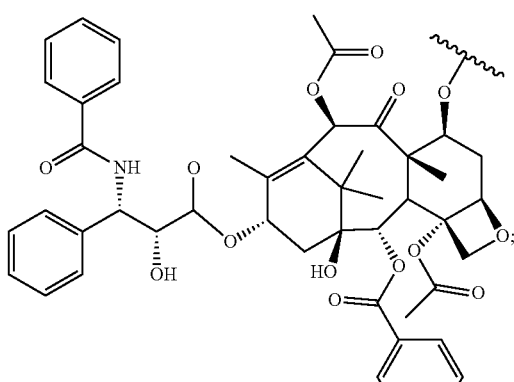

Paclitaxel

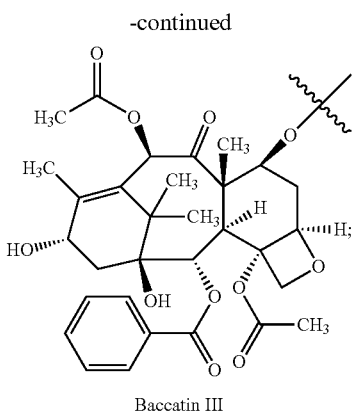

Baccatin III

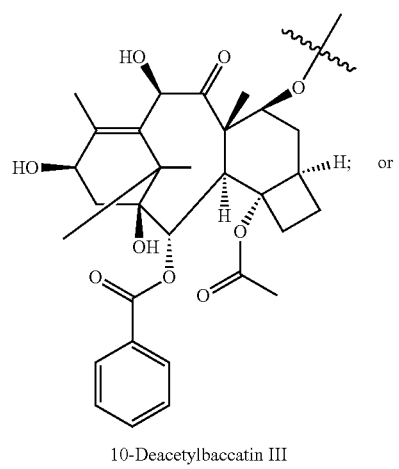

10-Deacetylbaccatin III

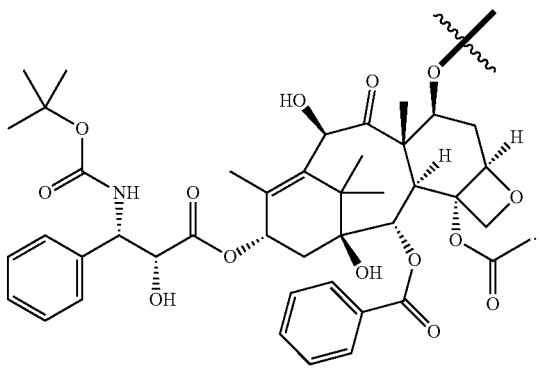

Docetaxel

13. The compound of claim 12, wherein the linker is selected from:

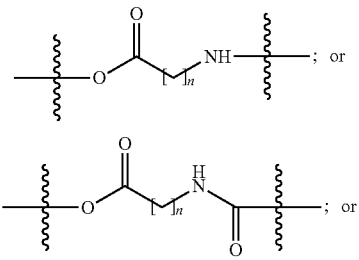

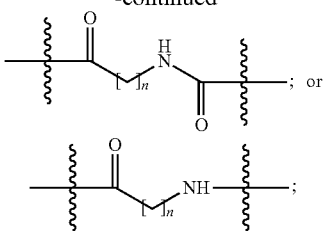

wherein n is an integer; and
R is selected from —O⁻, —OH, —NH$_2$, —NH-alkyl, —N(alkyl)$_2$, —NH$_2$—R1, —N(R1)$_2$ or —NR1R2;
R1 is $C_1$-$C_{24}$ alkyl; and
R2 is hydrogen or $C_1$-$C_{24}$ alkyl.

14. The compound of claim 13, wherein:
R is selected from —O⁻, —OH, —NH-methyl;
the linker is selected from glycine, beta-alanine, gamma-aminobutyric acid (GABA).

15. A pharmaceutical composition comprising:
the compound of claim 1; and
a pharmaceutically acceptable carrier.

16. A method of treating cancer, comprising:
administering the compound of claim 1 to a subject having cancer.

17. The method of claim 16, wherein the cancer is Kaposi sarcoma, cervical cancer, pancreatic cancer, ovarian cancer, breast cancer, bladder cancer, prostate cancer, melanoma, esophageal cancer, and/or lung cancer.

18. A method of studying of a microtubule, comprising:
contacting the compound of claim 1 to a microtubule in a cell; and
monitoring a functionality of the microtubule in the cell.

19. The method of claim 18, further comprising visualizing or detecting the microtubule from fluorescence of the compound attached to the microtubule.

20. A method of studying P-glycoprotein, comprising:
contacting the P-glycoprotein, cell having the P-glycoprotein, with the compound of claim 1; and
monitoring efflux or no efflux of one or more substances from a cell having the P-glycoprotein.

21. The method of claim 20, further comprising visualizing or detecting the efflux or no efflux of the compound from the cell from fluorescence of the compound.

* * * * *